United States Patent
Mosher et al.

(10) Patent No.: US 10,406,199 B2
(45) Date of Patent: *Sep. 10, 2019

(54) LISINOPRIL FORMULATIONS

(71) Applicant: Silvergate Pharmaceuticals, Inc., Greenwood Village, CO (US)

(72) Inventors: Gerold L. Mosher, Kansas City, MO (US); David W. Miles, Kansas City, MO (US)

(73) Assignee: SILVERGATE PHARMACEUTICALS, INC., Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/295,482

(22) Filed: Mar. 7, 2019

(65) Prior Publication Data

US 2019/0201475 A1 Jul. 4, 2019

Related U.S. Application Data

(63) Continuation of application No. 16/053,164, filed on Aug. 2, 2018, now Pat. No. 10,265,370, which is a continuation of application No. 15/805,934, filed on Nov. 7, 2017, now Pat. No. 10,039,800, which is a continuation of application No. 15/483,691, filed on Apr. 10, 2017, now Pat. No. 9,814,751, which is a continuation of application No. 15/268,095, filed on Sep. 16, 2016, now Pat. No. 9,616,096, which is a continuation of application No. 14/934,752, filed on Nov. 6, 2015, now Pat. No. 9,463,183.

(60) Provisional application No. 62/249,011, filed on Oct. 30, 2015.

(51) Int. Cl.
| | |
|---|---|
| *A61K 38/05* | (2006.01) |
| *A61K 38/00* | (2006.01) |
| *A61K 9/00* | (2006.01) |
| *A61K 31/401* | (2006.01) |
| *A61K 47/26* | (2006.01) |
| *A61K 47/02* | (2006.01) |
| *A61K 45/06* | (2006.01) |
| *A61K 47/12* | (2006.01) |

(52) U.S. Cl.
CPC ............ *A61K 38/05* (2013.01); *A61K 9/0053* (2013.01); *A61K 9/0095* (2013.01); *A61K 31/401* (2013.01); *A61K 38/005* (2013.01); *A61K 45/06* (2013.01); *A61K 47/02* (2013.01); *A61K 47/12* (2013.01); *A61K 47/26* (2013.01)

(58) Field of Classification Search
CPC .... A61K 38/05; A61K 38/005; A61K 9/0053; A61K 31/401; A61K 47/26; A61K 9/0095; A61K 47/02; A61K 45/06; A61K 47/12

See application file for complete search history.

(56) References Cited

U.S. PATENT DOCUMENTS

| | | | |
|---|---|---|---|
| 4,374,829 A | 2/1983 | Harris et al. | |
| 4,472,380 A | 9/1984 | Harris et al. | |
| 4,510,083 A | 4/1985 | Blacklock et al. | |
| 4,743,450 A | 5/1988 | Harris et al. | |
| 4,793,998 A | 12/1988 | Murthy et al. | |
| 4,830,853 A | 5/1989 | Murthy et al. | |
| 4,931,430 A | 6/1990 | Sudilovsky et al. | |
| 5,049,553 A | 9/1991 | Sudilovsky | |
| 5,698,562 A | 12/1997 | Mendes et al. | |
| 6,028,222 A | 2/2000 | Dietlin et al. | |
| 6,300,361 B1 | 10/2001 | Vivilecchia et al. | |
| 6,300,362 B1 | 10/2001 | Vivilecchia et al. | |
| 6,413,988 B1 | 7/2002 | De | |
| 6,509,350 B2 | 1/2003 | Vivilecchia et al. | |
| 6,790,861 B2 | 9/2004 | Vivilecchia et al. | |
| 6,869,963 B2 | 3/2005 | Patel et al. | |
| 6,977,257 B2 | 12/2005 | Parab et al. | |
| 7,101,888 B2 | 9/2006 | Reo et al. | |
| 7,605,148 B2 | 10/2009 | Batta et al. | |
| 8,153,824 B2 | 4/2012 | Sesha | |
| 8,568,747 B1 | 10/2013 | Rajewski et al. | |
| 8,778,366 B2 | 7/2014 | Rajewski et al. | |
| 8,927,028 B2 | 1/2015 | Grenier et al. | |
| 9,463,183 B1* | 10/2016 | Mosher | A61K 47/12 |
| 9,616,096 B1* | 4/2017 | Mosher | A61K 47/12 |
| 9,814,751 B2* | 11/2017 | Mosher | A61K 47/12 |
| 10,039,800 B2* | 8/2018 | Mosher | A61K 47/12 |
| 2004/0171669 A1 | 9/2004 | Chenevier | |
| 2004/0258757 A1 | 12/2004 | Bosch et al. | |
| 2006/0094760 A1 | 5/2006 | Fawzy et al. | |
| 2007/0265344 A1 | 11/2007 | Strobel et al. | |

(Continued)

FOREIGN PATENT DOCUMENTS

| | | |
|---|---|---|
| CA | 1275350 C | 10/1990 |
| EP | 2903690 A1 | 8/2015 |

(Continued)

OTHER PUBLICATIONS

Christian Brilla, et al, Lisinopril-Mediated Regression of Myocardial Fibrosis in Patients with Hypertensive Heart Disease, 102 Circulation 1388 (Year: 2000).*

(Continued)

*Primary Examiner* — Sean M Basquill

(74) *Attorney, Agent, or Firm* — Wilson Sonsini Goodrich & Rosati

(57) ABSTRACT

Provided herein are stable lisinopril oral liquid formulations. Also provided herein are methods of using lisinopril oral liquid formulations for the treatment of certain diseases including hypertension, heart failure and acute myocardial infarction.

20 Claims, 2 Drawing Sheets

(56) References Cited

U.S. PATENT DOCUMENTS

| | | | |
|---|---|---|---|
| 2008/0221156 A1* | 9/2008 | Spireas | A61K 9/1694 514/307 |
| 2008/0234291 A1 | 9/2008 | Francois et al. | |
| 2009/0269287 A1* | 10/2009 | Berta | A61K 8/73 424/52 |
| 2010/0222334 A1* | 9/2010 | Talamonti | A61K 9/0095 514/224.2 |
| 2011/0003798 A1* | 1/2011 | Okram | C07D 471/04 514/224.2 |
| 2014/0100260 A1 | 4/2014 | Rajewski et al. | |
| 2015/0148335 A1 | 5/2015 | Bova et al. | |
| 2015/0258027 A1 | 9/2015 | Rajewski et al. | |
| 2017/0119840 A1 | 5/2017 | Mosher et al. | |
| 2017/0209523 A1 | 7/2017 | Mosher et al. | |
| 2018/0078604 A1 | 3/2018 | Mosher et al. | |
| 2018/0339011 A1* | 11/2018 | Mosher | A61K 47/12 |

FOREIGN PATENT DOCUMENTS

| | | |
|---|---|---|
| WO | WO-9814196 A1 | 4/1998 |
| WO | WO-0145667 A2 | 6/2001 |
| WO | WO-02089775 A1 | 11/2002 |
| WO | WO-2007070843 A2 | 6/2007 |
| WO | WO-2009116078 A2 | 9/2009 |
| WO | WO-2011031462 A2 | 3/2011 |
| WO | WO-2011128783 A2 | 10/2011 |
| WO | WO-2012085249 A2 | 6/2012 |
| WO | WO-2014055667 A1 | 4/2014 |
| WO | WO-2014178065 A1 | 11/2014 |
| WO | WO-2017075368 A1 | 5/2017 |

OTHER PUBLICATIONS

Lisinopril "Lisinopril 1mg/ml Oral Liquid" retrieved from www.uspharmacist.com (Year: 2013).*

Mouin Seikaly, Hypertension in Children: An Update of Treatment Strategies, 19 Curr. Opin. Pediatr. 170 (Year: 2007).*

G.L. Nicolosi, et al, the Prognositc Value of Predischarge Quantitative Two-Dimensional Echocardiographic Measurements and the Effects of Early Lisinopril treatment on Left Ventricular Structure and Function After Acute Myocardial Infarction in the GISSI-3 Trial, 17 Eur. Heart J 1646 (Year: 1996).*

AAPS American Association of Pharmaceutical Scientists, Preliminary Program, 2011 AAPS Annual Meeting and Exposition, Washington, D.C., Oct. 23-27, 2011, 112 pages.

AAPS American Association of Pharmaceutical Scientists, selected pages from www.aaps.org, 12 pages.

Ahlin et al. Investigation of polymeric nanoparticles as carriers of enalaprilat for oral administration. Int'l. J Pharmaceutics 239:113-120 (2002).

Allen et al. Stability of alprazolam, chloroquine phosphate, cisapride, enalapril maleate, and hydralazine hydrochloride in extemporaneously compounded oral liquids. Am J. Health-Syst Pharm 55:1915-1920 (1998).

Allen. Formulations, Lisinopril 1-mg/mL, Sodium Citrate, and Citric Acid Oral Liquid. International Journal of Pharmaceutical Compounding 10(5):1 (Sep./Oct. 2006).

Allen Jr., Lloyd V., Formulations, Lisinopril 1-mg/mL, Sodium Citrate, and Citric Acid Oral Liquid. International Journal of Pharmaceutical Compounding, 10(5): 1 page, Sep./Oct. 2006.

Allen. Lisinopril 1 mg/mL oral liquid US Pharm. 38(2):36-37 (2013).

Al-Omari et al. Effect of the drug-matrix on the stability of enalapril maleate in tablet formulations. Journal of Pharmaceutical and Biomedical Analysis 25:893-902 (2001).

Beidel et al., Liquid dosage forms intended for pediatric use: Lisinopril & Meclizine. Department of Pharmaceutical Sciences, School of Pharmacy, Wilkes University, Wilkes-Barre, PA, presented at 2011 AAPS Meeting and Exposition, Oct. 26, 2011, Washington, D.C., 1 page.

Bhardwaj et al. Study of forced degradation behavior of enalapril maleate by LC and LC-MS and development of a validated stability-indicating assay method. Journal of Pharmaceutical and Biomedical Analysis 46:113-120 (2008).

Blowey. Update on the pharmacologic treatment of hypertension in pediatrics. Journal of Clinical Hypertension 14(6), 383-387 (2012).

Boukarim et al. Preservatives in liquid pharmaceutical preparations. The Journal of Applied Research 9(1 & 2):14-17 (2009).

Bourgault et al., Reference-based pricing of prescription drugs: exploring the equivalence of angiotensin-converting-enzyme inhibitors. CMAJ 161:255-60 (1999).

Brilla et al., Lisinopril-Mediated regression of myocardial fibrosis in patients with hypertensive heart disease. Circulation 102:1388-1393 (2000).

Cabot Corporation, "Influence of CAB-O-SIL® M-5P on the Angle of Repose and Flow Rates of Pharmaceutical Powders," 10 pages (2004).

Calabro et al. Hemodynamic effects of a single oral dose of enalapril among children with asymptomatic chronic mitral regurgitation. American Heart Journal 138(5, Pt. 1):955-961 (1999).

Decision, Instituting Post Grant Review of Claims 1-13, *KVK-TECH, Inc. and Flat Line Capital, LLC v. Silvergate Pharmaceuticals, Inc.*, Case No. PGR2017-00039, Patent Trial and Appeal Board, U.S. Pat. No. 9,463,183, entered Feb. 6, 2018, 22 pages.

Declaration of Benjamin Beidel, May 9, 2017, 4 pages.

Declaration of Dr. Arthur Kibbe, Ph.D., May 10, 2017, 61 pages.

Declaration of Jefferson Bohan, May 12, 2017, 6 pages.

Definition of Hypertension (1 page) retrieved from: http://medical-dictionary.thefreedictionary.com/hypertension (2008).

Delucchi et al., "Enalapril and prednisone in children with nephrotic-range proteinuria," Pediatric nephrology (Berlin, Germany) (2000), 14(12), 1088-91, Database: MEDLINE.

Drug Information on Enalapril (3 pages), 2001. retrieved from: http://www.accessdata.fda.gov/drugsatfda_docs/nda/2001/18-998s058_Vasotec.cfm.

drugs.com. Enalapril Tablets Soluble. Website [online]. [available online May 9, 2010] [retrieved on Jan. 16, 2014], 11 pages. Retrieved from the Internet< URL: https://web.archive.org/web/20100509220009/http://www.drugs.com/pro/enalapril-tablets-soluble.html>. Enalapril Tablets Soluble—Clinical Pharmacology; Indications and Usage for Enalapril Tablets Soluble; Enalapril Tablets Soluble Dosage and Administration.

European Patent Application No. 13844343.7 Extended European Search Report dated Feb. 19, 2016.

Glass et al. Stability considerations in liquid dosage forms extemporaneously prepared from commercially available products. J Pharm Sci 9(3):398-426 (2006).

Gulf Cooperation Council. The GCC Guidelines for Stability Testing of Drug Substances and Pharmaceutical Products. Publication [online]. Edition Two, 1428 H-2007 G [available online Jul. 2011] [retrieved on Feb. 3, 2014]. Retrieved from the Internet< URL: https://web.archive.org/web/20110726040053/http://www.ich.org/fileadmin/Public_Web_Site/ABOUT_ICH/Organisation/GCC/T opics under_Harmonisation/Stability.pdf>. page 22, 2.9 .3; p. 25, 2.9.7.

Handbook of Pharmaceutical Excipients, Fifth edition, edited by Raymond C. Rowe et al., London: Pharmaceutical Press, 2006, (monographs for citric acid monohydrate, sodium benzoate, sodium citrate, sodium hydroxide, and xylitol), 23 pages.

Harris, Daniel C. Exploring Chemical Analysis, 4th edition. New York:W.H. Freeman and Company, 2009 (Chapters 8,9,21 and 22), 105 pages.

Hensel et al. Transesterification reactions off parabens (Alkyl 4-Hydroxybenzoates) with polyols in aqueous solution. J Pharm Sci 84(1):115-119 (1995).

Hsu et al. Enalapril in Infants With Single Ventricle: Results of a Multicenter Randomized Trial. Circulation 122(4):333-340 (2010).

Hsu et al. Rationale and design of a trial of angiotensin-converting enzyme inhibition in infants with single ventricle. American Heart Journal 157(1):37-45 (2009).

Joint Motion for Adverse Judgment, *KVK-TECH, Inc. and Flat Line Capital, LLC v. Silvergate Pharmaceuticals, Inc.*, Case No. PGR2017-00039, Patent Trial and Appeal Board, U.S. Pat. No. 9,463,183, dated Apr. 16, 2018, 3 pages.

(56) References Cited

OTHER PUBLICATIONS

Kalaitzidis et al. Prehypertension: is it relevant for nephrologists? Kidney International 77:194-200 (2010).
Kibbe et al., Lisinopril as a liquid dosage form intended for pediatric use. Published Meeting Abstracts, American Association of Pharmaceutical Scientists, AAPS2011-002534, 2011, 1 page.
KVK-TECH, Inc. and Flat Line Capital, LLC (Petitioner) v. Silvergate Pharmaceuticals, Inc. (Patent Owner), Petition for Post Grant Review of U.S. Pat. No. 9,463,183, petition filed Jul. 10, 2017, 90 pages.
Li et al. Lessons learned from a pediatric clinical trial: The Pediatric Heart Network Angiotensin-Converting Enzyme Inhibition in Mitral Regurgitation Study. American Heart Journal 161(2):233-240 (2011).
Liern et al., "The additive antiproteinuric effect of Enalapril and Losartan to normotensive patients with pathology proteinuria," Nefrologia : publicacion oficial de la Sociedad Espanola Nefrologia (2004), 24(6), 553-8, Database: MEDLINE (with English abstract).
Lima et al., "Stability and in vitro release profile of enalapril maleate from different commercially available tablets: Possible therapeutic implications," Journ. Pharmac. and Biomed. Analysis, 47, pp. 934-937 (2008).
Lipshultz, "Exposure to anthracyclines during childhood causes cardiac injury," Seminars in Oncology (2006), 33(3, Suppl. 8), S8-S14., Database: CAPLUS, DOI:10.1053/j.seminoncol.2006.04.019.
Lisinopril Dihydrate. Definition, European Pharmacopoeia 5.0, 2005, 1922-1923, 2 pages.
Lisinopril liquid pediatrics. Google Search, 1 page, 2017.
Lisinopril "Lisinopril 1mg/ml Oral Liquid" retrieved from www.uspharmacist.com.
Ma et al., HPLC and LC-MS studies of the transesterification reaction of Methylparaben with twelve 3- to 6-carbon sugar alcohols and propylene glycol and the isomerization of the reaction products by acyl migration. Journal of Chromatograaphic Science, 40(3):170-177, 2002.
Meyers et al. Pharmacotherapy Review of Chronic Pediatric Hypertension. Clinical Therapeutics (2011), 33(10), 1331-1356. Database: CAPLUS, DOI:10.1016/j.clinthera.2011.09.003.
Miller et al., "Enalapril: a well-tolerated and efficacious agent for the paediatric hypertensive patient," Journal of hypertension. Supplement : official journal of the International Society of Hypertension (1986), 4(5), S413-6, Database: MEDLINE.
Miller et al., "Enalapril: a well-tolerated and efficacious agent for the pediatric hypertensive patient," Journal of cardiovascular pharmacology (1987), 10 Suppl 7S154-6, Database: MEDLINE.
Mir et al., "Effect of carvedilol on QT duration in pediatric patients with congestive heart failure," Clinical Drug Investigation (2004), 24(1), 9-15. Database: CAPLUS, DOI:10.2165/00044011-200424010-00002.
Momma, "ACE inhibitors in pediatric patients with heart failure," Paediatric drugs (2006), 8(1), 55-69, Database: MEDLINE.
Nahata and Morosco, Stability of Lisinopril in two liquid dosage forms. Ann Pharmacother, 38:396-399, 2004.
Nahata et al.Stability of enalapril maleate in three extemporaneously prepared oral liquids. Am. J. Health-Syst Pharm 55:1155-1157 (1998).
Nakamura et al., "The kinetic profiles of enalapril and enalaprilat and their possible developmental changes in pediatric patients with congestive heart failure," Clinical pharmacology and therapeutics (1994), 56(2), 160-8, Database: MEDLINE.
National institutes of Health. 'MedlinePius: Hypertension'. Website [online]. [available online May 20, 2012] [retrieved on Jan. 16, 2014], 5 pages. Retrieved from the Internet< URL:https://web.archive.org/web/20120520035026/http://www.nlm.nih.gov/medlineplus/ency/article/000468.htm>.
Nationwide Children's Hospital. 'Enalapril Oral Suspension' Publication [online]. Mar. 29, 2010 [retrieved on Jan. 14, 2014], 1 page. Retrieved from the Internet< URL:http://www.nationwidechildrens.org/Document/Get/78785>.

Niazi, Sarfaraz K. Handbook of Pharmaceutical Manufacturing Formulations: Liquid Products, vol. 3, Second edition. New York: Informa Healthcare USA, Inc., 2009, 400 pages.
Nicolosi et al., The prognostic value of predischarge quantitative two-dimensional echocardiographic measurements and the effects of early lisinopril treatment on left ventricular structure and function after acute myocardial infarction in the GISSI-3 trial. European Heart Journal, 17:1646-1656, 1996.
*Novartis AG* (Appellants) v. *Torrent Pharmaceuticals Limited, Apotex Inc., Mylan Pharmacuticals Inc.*, (Appellees), No. 2016-1352, Slip Opinion decided Apr. 12, 2017, 27 pages.
Nunn et al. Formulation of medicines for children. British Journal of Clinical Pharmacology, 59:6, pp. 674-676 (2005).
Order Dismissing Patent Owner's Request for Rehearing. *KVK-TECH, Inc. and Flat Line Capital, LLC* v. *Silvergate Pharmaceuticals, Inc.*, Case No. PGR2017-00039, Patent Trial and Appeal Board, U.S. Pat. No. 9,463,183, dated May 7, 2018, 3 pages.
Packer et al., Comparative effects of low and high doses of the angiotensin-converting enzyme inhibitor, lisinopril, on morbidity and mortality in chronic heart failure. Circulation, 100:2312-1218, 1999.
Patel et al., "Extemporaneous Dosage Form for Oral Liquids," Pharmacophore, vol. 2, No. 2, pp. 86-103 (2011).
PCT Patent Application No. PCT/US2013/063096 International Preliminary Report on Patentability dated Apr. 7, 2015.
PCT Patent Application No. PCT/US2013/063096 International Search Report Feb. 20, 2014.
PCT Patent Application No. PCT/US2013/063096 Written Opinion dated Feb. 20, 2014.
PCT Patent Application No. PCT/US2016/059348 International Search Report and Written Opinion dated Jan. 3, 2017.
Product Information of Bicitra, "Sodium Citrate and Citric Acid Oral Solution Usp." 2 pages.
Product Information of Ora-Sweet(1 page, 2013) retrieved from, http://www.stobec.com/documents/data/8196.pdf.
Proesmans et al., "Enalapril in children with Alport syndrome," Pediatric nephrology (Berlin, Germany) (2004), 19(3), 271-5, Database: MEDLINE.
Proesmans et al., long-term therapy with enalapril in patients with nephrotic-range proteinuriam, Pediatric nephrology (Berlin, Germany) (1996), 10(5), 587-9, Database: MEDLINE.
Prosemans et al., "Enalapril in pediatric patients with Alport syndrome: 2 years' experience," European Journal of Pediatrics (2000), 159(6), 430-433. Database: CAPLUS, DOI:10.1007/s004310051301.
Raia, et al., Angiotensin-converting enzyme inhibitors: A Comparative review. DPIC, The Annuals of Pharmacotherapy, 24:506-525, 1990.
Ramusovic et al., "Determination of enalapril and enalaprilat in small human serum quantities for pediatric trials by HPLC-tandem mass spectrometry," Biomedical Chromatography (2012), 26(6), 697-702. Database: CAPLUS, DOI:10.1002/bmc.1716.
Rezende et al., "Stability and Compatibility Study on Enalapril Maleate Using Thermoanalytical Techniques," Journ Thermal Analysis and Calorimetry, 93:3, pp. 881-886 (2008).
"Rippley et al., "Pharmacokinetic Assessment of an Oral Enalapril Suspension for Use in Children," Biopharmaceutics & Drug Disposition 21:339-344 (2000).".
Rokicki, "Use of converting enzyme inhibitors in children. I. General remarks," Wiadomosci lekarskie (Warsaw, Poland : 1960) (1997), 50(1-3), 28-31, Database: MEDLINE (with English abstract).
Rose et al., Stability of Lisinopril syrup (2 mg/mL) extemporaneously compounded from tablets. Int J Pharm Compd. 4(5):398-399 (2000).
Russell, Craig Allen, Paediatric Drug Development:—Reformulation, In Vitro, Genomic and in Vivo Evaluation. Thesis, Apr. 2014, 330 pages.
Sandoz, Limited. Amoxicillin 125 mg/5 ml Powder for Oral Suspension. Product brochure [online]. Jul. 2012 [retrieved on Jan. 17, 2014]. 3 pages. Retrieved from the Internet< URL:http://www.drugs.com/uklpdf/leaflet/196044.pdf>.
Seikaly. Hypertension in children: an update on treatment strategies. Current Opinion in Pediatrics, 19:170-177, 2007.

(56) References Cited

OTHER PUBLICATIONS

Silber et al., "Design and baseline characteristics for the ACE inhibitor after anthracycline (AAA) study of cardiac dysfunction in long-term pediatric cancer survivors," American Heart Journal (2001), 142(4), 577-585. Database: CAPLUS, DOI:10.1067/mhj.2001.118115.
Silber et al., "Enalapril to prevent cardiac function decline in long-term survivors of pediatric cancer exposed to anthracyclines," Journal of Clinical Oncology (2004), 22(5), 820-828. Database: CAPLUS, DOI:10.1200/JCO.2004.06.022.
Simončič et al., "Use of microcalorimetry in determination of stability of enalapril maleate and enalapril maleate table formulations," Int'l. Journ. Pharmaceutics, 342, pp. 145-151 (2007).
Sipahi et al. Effect of Antihypertensive Therapy on Incident Stroke in Cohorts with Prehypertensive Blood Pressure Levels: A Meta-Analysis of Randomized Controlled Trials, Stroke: Journal of the America! Heart Association [online], Dec. 8, 2011 (retrieved Jan. 16, 2014]. 10 pages. Retrieved from the Internet< URL:http://www.medpagetoday.com/upload/2011/12/9/Stroke-2011-Sipahi-STROKEAHA.111.636829.pdf>.
Sipahi et al., Effects of normal, pre-hypertensive, and hypertensive blood pressure levels on progression of coronary atherosclerosis, J. Am. Coll. Cardiol. 48, 833-838, 2006.
Sosnowska et al., "Stability of Extemporaneous Enalapril Maleate Suspensions for Pediatric Use Prepared from Commercially Available Tablets," Acta Poloniae Pharmaceutica, vol. 66, No. 3, pp. 321-326 (2009).
Garrett. Prediction of stability of drugs and pharmaceutical preparations. Journal of Pharmaceutical Sciences 51(9):811-833 (1962).
Judgment and Final Written Decision. *KVK-TECH, Inc. and Flat Line Capital, LLC v. Silvergate Pharmaceuticals, Inc.*, Case No. PGR2017-00039, Patent Trial and Appeal Board, U.S. Pat. No. 9,463,183, dated May 7, 2018, 3 pages.
Order Granting Joint Motion to Limit the Petition. *KVK-TECH, Inc. and Flat Line Capital, LLC v. Silvergate Pharmaceuticals, Inc.*, Case No. PGR2017-00039, Patent Trial and Appeal Board, U.S. Pat. No. 9,463,183, dated May 7, 2018, 3 pages.
Standing et al. Paediatric formulations-Getting to the heart of the problem. International Journal of Pharmaceutics (2005), 300(1-2), 56-66. Database: CAPLUS.
Stanisz, "Evaluation of stability of enalapril maleate in solid phase," Journ. Pharma. and Biomed. Analysis, 31, pp. 375-380 (2003).
Teva UK, Limited. Enalapril Maleate 2.5 mg, 5 mg, 10 mg and 20 mg Tablets. Product Brochure [online]. Mar. 2011 [retrieved on Jan. 14, 2014], 8 pages. Retrieved from the Internet< URL:http://www.drugs.com/uk/pdf/leaflet/213793.pdf>. col. 2, lines 70-76.
Thompson et al., Characterization of an entemporaneous liquid formulation of lisinopril. Am J Health Syst Pharm. 60(1):69-74 (2003).
Tian et al., Effect of organic anion-transporting polypeptide 1B1 (OATP1B1) polymorphism on the single- and multiple-dose pharmacokinetics of enalapril in healthy Chinese adult men Clinical Therapeutics, 33(5): 655 (2011).
Tuse et al., Stress degradation of Lisinopril as per ICH guidelines & characterisation. International Journal of Advances in Pharmaceutical Analysis, 4(2):47-52, 2014.
U.S. Appl. No. 13/670,355 Office Action dated Feb. 8, 2013.
U.S. Appl. No. 13/670,355 Office Action dated Jul. 30, 2013.
U.S. Appl. No. 13/914,452 Office Action dated Aug. 28, 2013.
U.S. Appl. No. 14/433,502 Office Action dated Dec. 29, 2016.
U.S. Appl. No. 14/934,752 First Action Interview dated Jan. 25, 2016.
U.S. Appl. No. 14/934,752 Office Action dated Apr. 26, 2016.
U.S. Appl. No. 15/081,603 First Action Interview dated Sep. 2, 2016.
U.S. Appl. No. 15/081,603 First Action Interview Office Action Summary dated Jan. 17, 2017.
U.S. Appl. No. 15/268,095 Office Action dated Oct. 13, 2016.
U.S. Appl. No. 15/483,691 Office Action dated Jun. 8, 2017.
U.S. Appl. No. 15/805,934 Office Action dated Jan. 26, 2018.
U.S. Appl. No. 16/053,164 Office Action dated Sep. 27, 2018.
Van Hecken et al. Absence of a pharmacokinetic interaction between enalapril and frusemide British Journal of Clinical Pharmacology, 1987, vol. 23:84-87.
Vasotec (Enalapril Maleate) Product Insert (2010) 5 pages (Best copy available).
Wang et al., "Eudragit E Accelerated the Diketopiperazine Formation of Enalapril Maleate Determined by Thermal FTIR Microspectroscopic Technique," Pharmaceutical Research, vol. 21, No. 11, Nov. 2004.
Webster et al., The Stability of Lisinopril as an extemporaneous syrup. Int J Pharm Compd. 1(5):352-353 (1997).
Wells et al., "A double-blind, placebo-controlled, dose-response study of the effectiveness and safety of enalapril for children with hypertension," Journal of Clinical Pharmacology (2002), 42(8), 870-880. Database: CAPLUS, DOI:10.1177/009127002401102786.
Wells et al., "The Pharmacokinetics of Enalapril in Children and Infants with Hypertension," J. Clin Pharmacol 41:1064-1074 (2001).
Wilkes University, School of Pharmacy, Poster presentations, spreadsheet, 2 pages.
Williams et al, "Factors affecting growth in infants with single ventricle physiology: a report from the Pediatric Heart Network Infant Single Ventricle Trial," The Journal of Pediatrics (2011), 159(6), 1017-22.e2, Database: MEDLINE.

* cited by examiner

LISINOPRIL FORMULATIONS

CROSS-REFERENCE

This application is a continuation of U.S. patent application Ser. No. 16/053,164, filed Aug. 2, 2018, which is a continuation of U.S. patent application Ser. No. 15/805,934, filed Nov. 7, 2017 (now U.S. Pat. No. 10,039,800, issued on Aug. 7, 2018), which is a continuation of U.S. patent application Ser. No. 15/483,691, filed Apr. 10, 2017 (now U.S. Pat. No. 9,814,751, issued on Nov. 14, 2017), which is a continuation of U.S. patent application Ser. No. 15/268,095, filed Sep. 16, 2016 (now U.S. Pat. No. 9,616,096, issued Apr. 11, 2017), which is a continuation of U.S. patent application Ser. No. 14/934,752, filed Nov. 6, 2015 (now U.S. Pat. No. 9,463,183, issued Oct. 11, 2016), which claims the benefit of U.S. Provisional Patent Application No. 62/249,011, filed Oct. 30, 2015, all of which are incorporated herein by reference in their entirety.

BACKGROUND OF THE INVENTION

Hypertension, or high blood pressure, is a serious health issue in many countries. According to the National Heart Blood and Lung Institute, it is thought that about 1 in 3 adults in the United States alone have hypertension. Left unchecked, hypertension is considered a substantial risk factor for cardiovascular and other diseases including coronary heart disease, myocardial infarction, congestive heart failure, stroke and kidney failure. Hypertension is classified as primary (essential) hypertension or secondary hypertension. Primary hypertension has no known cause and may be related to a number of environmental, lifestyle and genetic factors such as stress, obesity, smoking, inactivity and sodium intake. Secondary hypertension can be caused by drug or surgical interventions or by abnormalities in the renal, cardiovascular or endocrine system.

A number of antihypertensive drugs are available for treating hypertension. Various therapeutic classes of antihypertensive drugs include alpha-adrenergic blockers, beta-adrenergic blockers, calcium-channel blockers, hypotensives, mineralcorticoid antagonists, central alpha-agonists, diuretics and rennin-angiotensin-aldosterone inhibitors which include angiotensin II receptor antagonists (ARB) and angiotensin-converting enzyme (ACE) inhibitors. Angiotensin-converting enzyme (ACE) inhibitors inhibit angiotensin-converting enzyme (ACE), a peptydyl dipeptidase that catalyzes angiotension I to angiotension II, a potent vasoconstrictor involved in regulating blood pressure.

Lisinopril is a drug belonging to the angiotensin-converting enzyme (ACE) inhibitor class of medications. Lisinopril IUPAC name is $N^2$-[(1S)-1-carboxy-3-phenylpropyl]-L-lysyl-L-proline. Its structural formula is as follows:

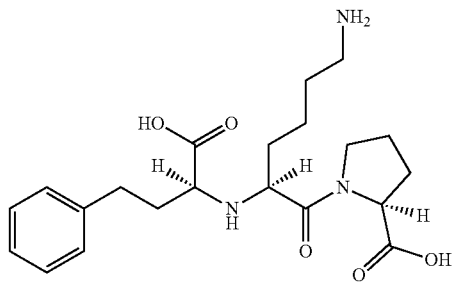

Lisinopril

Lisinopril is currently administered in the form of oral tablets, (e.g., Prinivil®, Zestril®). In addition to the treatment of hypertension, lisinopril tablets have been used for the treatment of heart failure and acute myocardial infarction.

SUMMARY OF THE INVENTION

Provided herein are lisinopril oral liquid formulations. In one aspect, the lisinopril oral liquid formulation comprises (i) lisinopril or a pharmaceutically acceptable salt or solvate thereof, (ii) a sweetener that is xylitol, (iii) a buffer comprising citric acid (iv) a preservative that is sodium benzoate, and (v) water; wherein the pH of the formulation is between about 4 and about 5; and wherein the formulation is stable at about 25±5° C. for at least 12 months.

In some embodiments, the lisinopril is lisinopril dihydrate. In some embodiments, the formulation further comprises a flavoring agent. In some embodiments, the formulation further comprises a second sweetener. In some embodiments, the second sweetener is sodium saccharin or sucralose. In some embodiments, the pH is about 4.9. In some embodiments, the formulation is stable at about 25±5° C. for at least 18 months. In some embodiments, the formulation is stable at about 25±5° C. for at least 24 months. In some embodiments, the buffer further comprises sodium citrate.

In some embodiments, the amount of lisinopril or a pharmaceutically acceptable salt or solvate thereof is about 0.8 to about 1.2 mg/ml. In some embodiments, the amount of xylitol is about 140 to about 160 mg/ml. In some embodiments, the amount of citric acid in the buffer is about 0.5 to about 1.2 mg/ml. In some embodiments, the amount of sodium citrate in the buffer is about 1.2 to about 1.7 mg/ml. In some embodiments, the amount of the sodium benzoate is about 0.5 to about 1.2 mg/ml.

In one aspect, the lisinopril oral liquid formulation comprises (i) about 1 mg/ml lisinopril or a pharmaceutically acceptable salt or solvate thereof, (ii) about 150 mg/ml of a sweetener that is xylitol, (iii) a buffer comprising about 0.86 mg/ml citric acid, (iv) about 0.8 mg/ml of a preservative that is sodium benzoate; and (v) water; wherein the pH of the formulation is between about 4 and about 5; and wherein the formulation is stable at about 25±5° C. for at least 12 months.

In some embodiments, the lisinopril is lisinopril dihydrate. In some embodiments, the formulation further comprises a flavoring agent. In some embodiments, the formulation further comprises a second sweetener. In some embodiments, the second sweetener is sodium saccharin or sucralose. In some embodiments, the pH is about 4.9. In some embodiments, the formulation is stable at about 25±5° C. for at least 18 months. In some embodiments, the formulation is stable at about 25±5° C. for at least 24 months. In some embodiments, the buffer further comprises sodium citrate. In some embodiments, the buffer further comprises about 1.44 mg/ml sodium citrate.

In some embodiments, the amount of lisinopril or a pharmaceutically acceptable salt or solvate thereof is about 0.5 to about 1% (w/w of solids). In some embodiments, the amount of xylitol is about 95 to about 98% (w/w of solids). In some embodiments, the amount of citric acid in the buffer is about 0.3 to about 0.7% (w/w of solids). In some embodiments, the amount of sodium citrate in the buffer is about 0.7 to about 1.3% (w/w of solids). In some embodiments, the amount of sodium benzoate is about 0.4 to about 1.2% (w/w of solids).

In another aspect, the lisinopril oral liquid formulation comprises (i) about 0.7% (w/w of solids) lisinopril or a pharmaceutically acceptable salt or solvate thereof, (ii) about 97.3% (w/w of solids) of a sweetener that is xylitol, (iii) a buffer comprising about 0.01 molar citrate, (iv) about 0.52% (w/w of solids) of a preservative that is sodium benzoate, and (v) water; wherein the pH of the formulation is between about 4 and about 5; and wherein the formulation is stable at about 25±5° C. for at least 12 months.

In some embodiments, the lisinopril is lisinopril dihydrate. In some embodiments, the formulation further comprises a flavoring agent. In some embodiments, the formulation further comprises a second sweetener. In some embodiments, the second sweetener is sodium saccharin or sucralose. In some embodiments, the pH is about 4.9. In some embodiments, the formulation is stable at about 25±5° C. for at least 18 months. In some embodiments, the formulation is stable at about 25±5° C. for at least 24 months. In some embodiments, the buffer comprises citric acid and sodium citrate.

In another aspect, the lisinopril oral liquid formulation consists of (i) about 1 mg/ml lisinopril or a pharmaceutically acceptable salt or solvate thereof, (ii) about 150 mg/ml of a sweetener that is xylitol, (iii) a buffer comprising about 0.86 mg/ml citric acid and about 1.44 mg/ml sodium citrate, (iv) about 0.8 mg/ml of a preservative that is sodium benzoate, (v) and water; wherein the pH of the formulation is between about 4 and about 5 adjusted by sodium hydroxide or hydrochloric acid; and wherein the formulation is stable at about 25±5° C. for at least 12 months. In some embodiments, the formulation is stable at about 25±5° C. for at least 24 months. In some embodiments, the pH is about 4.9.

Also provided herein are methods of treating hypertension comprising administering to a patient in need thereof a lisinopril oral liquid formulation described herein. In some embodiments, the hypertension is primary (essential) hypertension. In some embodiments, the hypertension is secondary hypertension. In some embodiments, the subject with hypertension has blood pressure values greater than or equal to 140/90 mmm Hg.

Also provided herein are methods of treating prehypertension comprising administering to a patient in need thereof a lisinopril oral liquid formulation described herein. In some embodiments, the subject with prehypertension has blood pressure values of about 120-139/80-89 mm Hg.

Also provided herein are methods of treating heart failure or acute myocardial infarction comprising administering to a patient in need thereof a lisinopril oral liquid formulation described herein.

In some embodiments, the subject is an adult. In some embodiments, the subject is elderly. In some embodiments, the subject is a child. In some embodiments, the lisinopril oral liquid formulation is administered to the subject in a fasted state. In some embodiments, the lisinopril oral liquid formulation is administered to the subject in a fed state.

In some embodiments, the lisinopril oral liquid formulation is further administered in combination with an agent selected from the group consisting of diuretics, beta blockers, alpha blockers, mixed alpha and beta blockers, calcium channel blockers, angiotensin II receptor antagonists, ACE inhibitors, aldosterone antagonists, and alpha-2 agonists.

Also provided herein is a process for preparing a stable oral liquid formulation comprising lisinopril, xylitol, a buffer, and sodium benzoate, the process which comprises the step of adding about 0.86 mg/ml anhydrous citric acid, about 1.44 mg/ml anhydrous sodium citrate, about 0.80 mg/ml sodium benzoate, about 1.09 mg/ml lisinopril dihydrate, and about 150 mg/ml xylitol to water; adjusting the volume to the desired volume by adding more water; and adjusting the pH to 4.9 by adding sodium hydroxide or hydrochloric acid.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
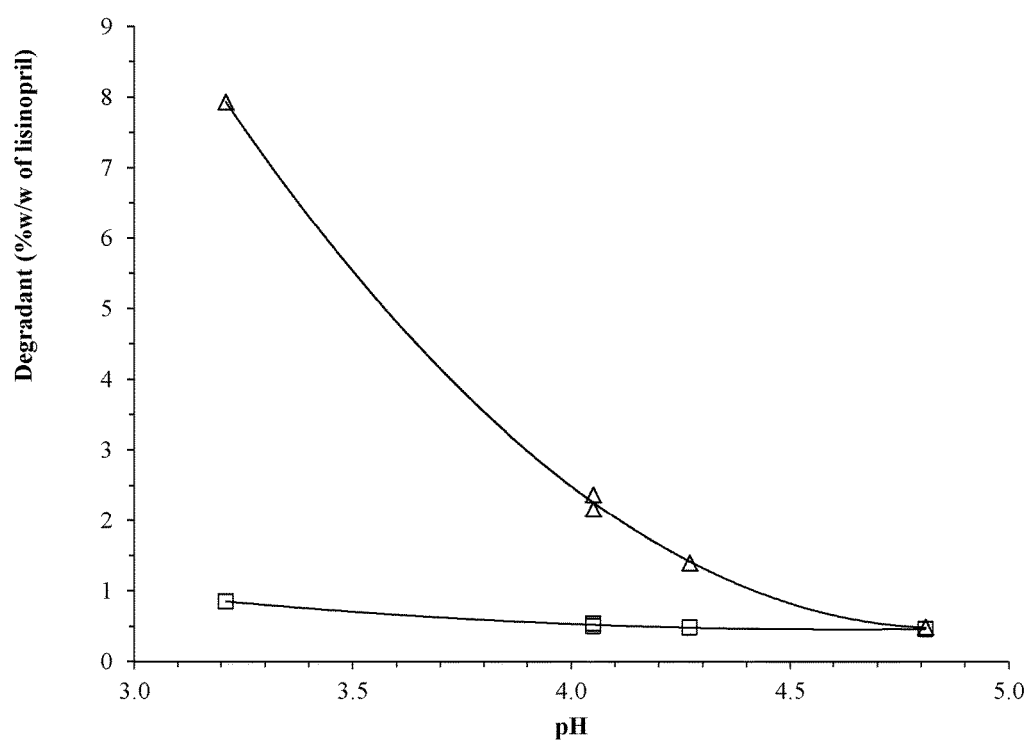
FIG. 1: Degradant formation in lisinopril formulations after 145 hours at 60° C. (Δ-Lisinopril diketopiperazine, □-hydrolysate).

Provided herein are stable lisinopril oral liquid formulations. Also provided herein are stable lisinopril powder formulations for reconstitution for oral liquid administration. These lisinopril formulations described herein are useful for the treatment of hypertension, prehypertension, heart failure as well as acute myocardial infarction. The formulations are advantageous over conventional solid dosage administration of lisinopril ranging from ease of administration, accuracy of dosing, accessibility to additional patient populations such as to children and the elderly, and an increased patient compliance to medication.

It is generally known that certain segments of the population have difficulty ingesting and swallowing solid oral dosage forms such as tablets and capsules. As many as a quarter of the total population has this difficulty. Often, this leads to non-compliance with the recommended medical therapy with the solid dosage forms, thereby resulting in rending the therapy ineffective. Further, solid dosage forms are not recommended for children or elderly due to increased risk in choking.

Furthermore, the dose of lisinopril to be given to children is calculated according to the child's weight. When the calculated dose is something other than the amount present in one or more intact solid dosage forms, the solid dosage form must be divided to provide the correct dose. This leads to inaccurate dosing when solid dosages forms, such as tablets, are compounded to prepare other formulations for children.

For lisinopril, the current solution to overcoming the use of the tablet form is for a compounding pharmacist to pulverize and crush the lisinopril tablet(s) into a powder via mortar and pestle and reconstitute the powder in some liquid form. However forming a lisinopril oral liquid in this fashion has significant drawbacks including large variability in the actual dosage, incomplete solubilizing of the lisinopril tablet in the liquid, rapid instability, inconsistent formulation methods per compounding pharmacy, and a number of other potential issues. The crushed tablet liquid formulation may also be potentially unsafe due to contamination with residual drugs and other substances from the mortar and pestle or other crushing agent.

The present embodiments provide a safe and effective oral administration of lisinopril for the treatment of hypertension and other disorders. In particular, the embodiments provide stable lisinopril oral liquid formulations as well as lisinopril powder formulations for reconstitution for oral liquid administration.

As used herein, "lisinopril" refers to lisinopril base, its salt, or solvate or derivative or isomer or polymorph thereof. Suitable compounds include the free base, the organic and inorganic salts, isomers, isomer salts, solvates, polymorphs, complexes etc. U.S. Pat. Nos. 4,374,829, 4,472,380, and CA 1,275,350 disclose exemplary methods in the preparation of lisinopril. In some embodiments, the lisinopril used in the formulations described herein is a lisinopril salt. In some instances, the lisinopril used in the formulations described herein is a lisinopril hydrate. In some instances, the lisinopril used in the formulations described herein is lisinopril monohydrate. In some instances, the lisinopril used in the formulations described herein is lisinopril dihydrate.

Other ACE inhibitors are contemplated in the formulations within and include but are not limited to quinapril, indolapril, ramipril, perindopril, benazepril, imidapril, zofenopril, trandolapril, fosinopril, captopril, and their salts, solvates, derivatives, polymorphs, complexes, thereof.

Lisinopril Oral Liquid Formulations

Oral liquids include, but are not limited to, solutions (both aqueous and nonaqueous), suspensions, emulsions, syrups, slurries, juices, elixirs, dispersions, and the like. It is envisioned that solution/suspensions are also included where certain components described herein are in a solution while other components are in a suspension.

In one aspect, the lisinopril oral liquid formulation described herein comprise lisinopril, a preservative, a sweetening agent, a buffer, and water. In one embodiment, the sweetening agent is xylitol. In some embodiments, the sweetening agent is sucralose. In some embodiments, the sweetener is saccharin. In another embodiment, the preservative is sodium benzoate. In yet another embodiment, the preservative is one or more paraben preservatives. In yet another embodiment, the buffer comprises citric acid. In yet another embodiment, the buffer comprises citric acid and sodium citrate. In yet another embodiment, the buffer comprises phosphoric acid or salts thereof. In one aspect, the lisinopril oral liquid formulation described herein comprises lisinopril, xylitol, sodium citrate, citric acid, sodium benzoate, and water. In some embodiments, the lisinopril oral liquid formulation herein further comprises a flavoring agent.

In some embodiments, lisinopril is present in about 0.8 mg/ml to about 1.2 mg/ml in the oral liquid formulation. In other embodiments, lisinopril is present in about 0.8 mg/ml, 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/ml, about 0.91 mg/ml, about 0.92 mg/ml, about 0.93 mg/ml, about 0.94 mg/ml, about 0.95 mg/ml, about 0.96 mg/ml, about 0.97 mg/ml, about 0.98 mg/ml, about 0.99 mg/ml, about 1 mg/ml, about 1.01 mg/ml, about 1.02, mg/ml, about 1.03 mg/ml, about 1.04 mg/ml, about 1.05 mg/ml, about 1.06 mg/ml, about 1.07 mg/ml, about 1.08 mg/ml, about 1.09 mg/ml, about 1.1 mg/ml, about 1.11 mg/ml, about 1.12, mg/ml, about 1.13 mg/ml, about 1.14 mg/ml, about 1.15 mg/ml, about 1.16 mg/ml, about 1.17 mg/ml, about 1.18 mg/ml, about 1.19 mg/ml, or about 1.2 mg/ml in the liquid oral formulation. In some embodiments, lisinopril is present in about 1 mg/ml in the oral liquid formulation.

In some embodiments, lisinopril is present in about 0.5% w/w to about 5% w/w of the solids in the oral liquid formulation. In other embodiments, Lisinopril is present in about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, or about 5% w/w of the solids in the oral liquid formulation. In some embodiments, lisinopril is present in about 0.5% w/w to about 1% w/w of the solids in the oral liquid formulation. In some embodiments, lisinopril is present in about 0.6% w/w to about 0.8% w/w of the solids in the oral liquid formulation. In some embodiments, lisinopril is present in about 0.7% w/w of the solids in the oral liquid formulation.

In some embodiments, lisinopril is present in about 10% w/w to about 25% w/w of the solids in the oral liquid formulation. In other embodiments, lisinopril is present in about 10% w/w, about 10.5% w/w, about 11% w/w, about 11.5% w/w, about 12% w/w, about 12.5% w/w, about 13% w/w, about 13.5% w/w, about 14% w/w, about 14.5% w/w, about 15% w/w, about 15.5% w/w, about 16% w/w, about 16.5% w/w, about 17% w/w, about 17.5% w/w, about 18% w/w, about 18.5% w/w, about 19% w/w, about 19.5% w/w, about 20% w/w, about 20.5% w/w, about 21% w/w, about 21.5% w/w, about 22% w/w, about 22.5% w/w, about 23% w/w, about 23.5% w/w, about 24% w/w, about 24.5% w/w, or about 25% w/w of the solids in the oral liquid formulation. In some embodiments, lisinopril is present in about 14% w/w to about 16% w/w of the solids in the oral liquid formulation. In some embodiments, lisinopril is present in about 17% w/w to about 19% w/w of the solids in the oral liquid formulation. In some embodiments, lisinopril is present in about 20% w/w to about 22% w/w of the solids in the oral liquid formulation.

Sweetener in the Lisinopril Oral Liquid Formulations

Sweeteners or sweetening agents include any compounds that provide a sweet taste. This includes natural and synthetic sugars, natural and artificial sweeteners, natural extracts and any material that initiates a sweet sensation in a subject. In some embodiments, a solid/powder sweetener is used in the oral liquid formulation described herein. In other embodiments, a liquid sweetener is used in the oral liquid formulation described herein.

Sugars illustratively include glucose, fructose, sucrose, xylitol, tagatose, sucralose, maltitol, isomaltulose, Isomalt™ (hydrogenated isomaltulose), lactitol, sorbitol, erythritol, trehalose, maltodextrin, polydextrose, and the like. Other sweeteners illustratively include glycerin, inulin, erythritol, maltol, acesulfame and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweeteners can be used in the form of crude or refined products such as hydrogenated starch hydrolysates, maltitol syrup, high fructose corn syrup, etc., and as branded products, e.g., Sweet Am™ liquid (Product Code 918.003-propylene glycol, ethyl alcohol, and proprietary artificial flavor combination, Flavors of North America) and Sweet Am™ powder (Product Code 918.005—maltodextrin, sorbitol, and fructose combination and Product Code 918.010—water, propylene glycol, sorbitol, fructose, and proprietary natural and artificial flavor combination, Flavors of North America), ProSweet™ (1-10% proprietary plant/vegetable extract and 90-99% dextrose combination, Viriginia Dare), Maltisweet™ (maltitol solution, Ingredion), Sorbo™ (sorbitol and sorbitol/xylitol solution, SPI Polyols), Invertose™ (high fructose corn syrup, Ingredion), Rebalance M60 and X60 (sucralose and maltodextrin, Tate and Lyle), and Ora-Sweet® sugar-free flavored syrup (Paddock Laboratories, Inc.). Sweeteners can be used singly or in combinations of two or more. Suitable concentrations of different sweeteners can be selected based on published information, manufacturers' data sheets and by routine testing.

In some embodiments, the lisinopril oral liquid formulation described herein comprises a sweetening agent. In some embodiments, the sweetening agent is sucralose. In some embodiments, the sweetening agent is xylitol. In some embodiments, the sweetener is saccharin.

In some embodiments, the sweetening agent is xylitol. In some embodiments, xylitol is present in about 140 mg/ml to about 160 mg/ml in the oral liquid formulation. In other embodiments, xylitol is present in about 140 mg/ml, about 141 mg/ml, about, 142 mg/ml, about 143 mg/ml, about 144 mg/ml, about 145 mg/ml, about 146 mg/ml, about 147 mg/ml, about 148 mg/ml, about 149 mg/ml, about 150 mg/ml, about 151 mg/ml, about 152 mg/ml, about 153 mg/ml, about 154 mg/ml, about 155 mg/ml, about 156 mg/ml, about 157 mg/ml, about 158 mg/ml, about 159 mg/ml, or about 160 mg/ml in the oral liquid formulation. In some embodiments, xylitol is present in about 150 mg/ml in the oral liquid formulation.

In some embodiments, xylitol is present in about 80% w/w to about 99% w/w of the solids in the oral liquid formulation. In other embodiments, xylitol is present in about 80% w/w, about 81% w/w, about 82% w/w, about 83% w/w, about 84% w/w, about 85% w/w, about 86% w/w, about 87% w/w, about 88% w/w, about 89% w/w, about 90% w/w, about 91% w/w, about 92% w/w, about 93% w/w, about 94% w/w, about 95% w/w, about 96% w/w, about 97% w/w, about 98% w/w, about 99% w/w of the solids in the oral liquid formulation. In some embodiments, xylitol is present in about 96% w/w to about 98% w/w of the solids in the oral liquid formulation. In some embodiments, xylitol is present in about 97% w/w of the solids in the oral liquid formulation.

In some embodiments, the sweetening agent is sucralose. In some embodiments, sucralose is present in about 0.5 mg/ml to about 3 mg/ml in the oral liquid formulation. In other embodiments, sucralose is present in about 0.5 mg/ml, about 0.6 mg/ml, about 0.7 mg/ml, about 0.8 mg/ml, about 0.9 mg/ml, about 1 mg/ml, about 1.1 mg/ml, about, 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, or about 3 mg/ml in the oral liquid formulation. In some embodiments, sucralose is present in about 2 mg/ml in the oral liquid formulation. In some embodiments, sucralose is present in about 0.7 mg/mL in the oral liquid formulation.

In some embodiments, sucralose is present in about 10% w/w to about 40% w/w of the solids in the oral liquid formulation. In other embodiments, sucralose is present in about 10% w/w, about 10.5% w/w, about 11% w/w, about 11.5% w/w, about 12% w/w, about 12.5% w/w, about 13% w/w, about 13.5% w/w, about 14% w/w, about 14.5% w/w, about 15% w/w, about 15.5% w/w, about 16% w/w, about 16.5% w/w, about 17% w/w, about 17.5% w/w, about 18% w/w, about 18.5% w/w, about 19% w/w, about 19.5% w/w, about 20% w/w, about 20.5% w/w, about 21% w/w, about 21.5% w/w, about 22% w/w, about 22.5% w/w, about 23% w/w, about 23.5% w/w, about 24% w/w, about 24.5% w/w, about 25% w/w, about 25.5% w/w, about 26% w/w, about 26.5% w/w, about 27% w/w, about 27.5% w/w, about 28% w/w, about 28.5% w/w, about 29% w/w, about 29.5% w/w, about 30% w/w, about 30.5% w/w, about 31% w/w, about 31.5% w/w, about 32% w/w, about 32.5% w/w, about 33% w/w, about 33.5% w/w, about 34% w/w, about 34.5% w/w, about 35% w/w, about 35.5% w/w, about 36% w/w, about 36.5% w/w, about 37% w/w, about 37.5% w/w, about 38% w/w, about 38.5% w/w, about 39% w/w, about 39.5% w/w, or about 40% w/w of the solids in the oral liquid formulation. In some embodiments, sucralose is present in about 34% w/w to about 35% w/w of the solids in the oral liquid formulation. In some embodiments, sucralose is present in about 28% w/w to about 30% w/w of the solids in the oral liquid formulation. In some embodiments, sucralose is present in about 12% w/w to about 15% w/w of the solids in the oral liquid formulation.

In some embodiments, the sweetening agent is saccharin. In some embodiments, saccharin is present in about 1 mg/ml to about 3 mg/ml in the oral liquid formulation. In other embodiments, saccharin is present in about 1 mg/ml, about 1.1 mg/ml, about, 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, or about 3 mg/ml in the oral liquid formulation. In some embodiments, saccharin is present in about 2 mg/ml in the oral liquid formulation.

In some embodiments, saccharin is present in about 1% w/w to about 3% w/w of the solids in the oral liquid formulation. In other embodiments, saccharin is present in about 1% w/w, 1.1% w/w, about 1.2% w/w, 1.3% w/w, about 1.4% w/w, 1.5% w/w, about 1.6% w/w, 1.7% w/w, about 1.8% w/w, 1.9% w/w, about 2% w/w, 2.1% w/w, about 2.2% w/w, 2.3% w/w, about 2.4% w/w, 2.5% w/w, about 2.6% w/w, 2.7% w/w, about 2.8% w/w, 2.9% w/w, or 3% w/w of the solids in the oral liquid formulation. In some embodiments, saccharin is present in about 1.7% w/w to about 1.9% w/w of the solids in the oral liquid formulation.

Preservative in the Lisinopril Oral Liquid Formulations

Preservatives include anti-microbials, anti-oxidants, and agents that enhance sterility. Exemplary preservatives include ascorbic acid, ascorbyl palmitate, BHA, BHT, citric acid, erythorbic acid, fumaric acid, malic acid, propyl gallate, sodium ascorbate, sodium bisulfate, sodium metabisulfite, sodium sulfite, parabens (such as methylparaben, ethylparaben, propylparaben, butylparaben and their salts), benzoic acid, sodium benzoate, potassium sorbate, vanillin, and the like.

In some embodiments, the lisinopril oral liquid formulation described herein comprises a preservative.

In some embodiments, the preservative is a paraben and the sweetener is not a sugar (such as, but not limited to glucose, fructose, sucrose, lactose, maltose) or a sugar alcohol (such as, but not limited to xylitol, mannitol, lactitol, maltitol, sorbitol).

In some embodiments, the preservative is sodium benzoate.

In some embodiments, modulation of the pH is desired to provide the best antimicrobial activity of the preservative, sodium benzoate. In some embodiments, the antimicrobial activity of sodium benzoate drops when the pH is increased above 5.

In some embodiments, the pH of the lisinopril oral liquid formulation described herein is less than about 5.1. In some embodiments, the pH of the lisinopril oral liquid formulation described herein is less than about 5. In some embodiments, the pH of the lisinopril oral liquid formulation described herein is between about 4 and about 5. In some embodiments, the pH of the lisinopril oral liquid formulation described herein is about 4, about 4.1, about 4.2, about 4.3, about 4.4, about 4.5, about 4.6, about 4.7, about 4.8, about 4.9, about 5, about 5.1, or about 5.2.

In some embodiments, sodium benzoate is present in about 0.5 mg/ml to about 1.2 mg/ml in the oral liquid formulation. In other embodiments, sodium benzoate is present in about 0.5 mg/ml, about 0.55 mg/ml, about 0.6 mg/ml, about 0.65 mg/ml, about 0.7 mg/ml, about 0.75 mg/ml, about 0.8 mg/ml, about 0.85 mg/ml, about 0.9 mg/ml, about 0.95 mg/ml, about 1 mg/ml, about 1.05 mg/ml, about 1.1 mg/ml, about 1.15 mg/ml, or about 1.2 mg/ml in the liquid oral formulation. In some embodiments, sodium benzoate is present in about 0.8 mg/ml in the oral liquid formulation.

In some embodiments, sodium benzoate is present in about 0.1% w/w to about 5% w/w of the powder formulation. In other embodiments, sodium benzoate is present in about 0.1% w/w, about 0.15% w/w, about 0.2% w/w, about 0.25% w/w, about 0.30% w/w, about 0.35% w/w, about 0.40% w/w, about 0.45% w/w, about 0.50% w/w, about 0.55% w/w, about 0.60% w/w, about 0.65% w/w, about 0.70% w/w, about 0.75% w/w, about 0.80% w/w, about 0.85% w/w, about 0.90% w/w, about 0.95% w/w, about 1% w/w, about 1.5% w/w, about 2% w/w, about 3% w/w, about 3.5% w/w, about 4% w/w, about 4.5% w/w, or about 5% w/w of the powder formulation. In some embodiments, sodium benzoate is present in about 0.4% w/w to about 1.2% w/w of the powder formulation. In some embodiments, sodium benzoate is present in about 0.52% w/w of the powder formulation.

In some embodiments, sodium benzoate is present in about 10% w/w to about 17% w/w of the solids in the oral liquid formulation. In other embodiments, sodium benzoate is present in about 10% w/w, about 10.5% w/w, about 11% w/w, about 11.5% w/w, about 12% w/w, about 12.5% w/w, about 13% w/w, about 13.5% w/w, about 14% w/w, about 14.5% w/w, about 15% w/w, about 15.5% w/w, about 16% w/w, about 16.5% w/w, or about 17% w/w of the solids in the oral liquid formulation. In some embodiments, sodium benzoate is present in about 12% w/w to about 17% w/w of the solids in the oral liquid formulation.

In some embodiments, sodium benzoate is present in an amount sufficient to provide antimicrobial effectiveness to the lisinopril oral liquid formulation described herein (see table D-1)

In some embodiments, the preservative is a paraben. In some embodiments, the preservative is a mixture of parabens. In some embodiments, the paraben or mixture of parabens is present in about 0.1 mg/ml to about 2 mg/ml in the oral liquid formulation. In other embodiments, the paraben or mixture of parabens is present in about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1 mg/ml, about 1.1 mg/ml, about 1.2 mg/ml, about 1.3 mg/ml, about 1.4 mg/ml, or about 1.5 mg/ml, about 1.6 mg/ml, about 1.7 mg/ml, about 1.8 mg/ml, about 1.9 mg/ml, or about 2 mg/ml in the liquid oral formulation. In some embodiments, the paraben or mixture of parabens is present in about 1.6 mg/ml to about 2 mg/ml in the oral liquid formulation. In some embodiments, the paraben or mixture of parabens is present in about 1.6 mg/ml to about 1.8 mg/ml in the oral liquid formulation. In some embodiments, the paraben or mixture of parabens is present in about 0.1 mg/ml to about 0.2 mg/ml in the oral liquid formulation.

In some embodiments, the paraben or mixture of parabens is present in about 2% w/w to about 30% w/w of the solids in the oral liquid formulation. In other embodiments, the paraben or mixture of parabens is present in about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, or about 30% w/w of the solids in the oral liquid formulation. In some embodiments, the paraben or mixture of parabens is present in about 2% w/w to about 3% w/w of the solids in the oral liquid formulation. In some embodiments, the paraben or mixture of parabens is present in about 23% w/w to about 26% w/w of the solids in the oral liquid formulation. In some embodiments, the paraben or mixture of parabens is present in about 26% w/w to about 30% w/w of the solids in the oral liquid formulation.

Sweetener and Preservative Incompatibility

Figure 2:
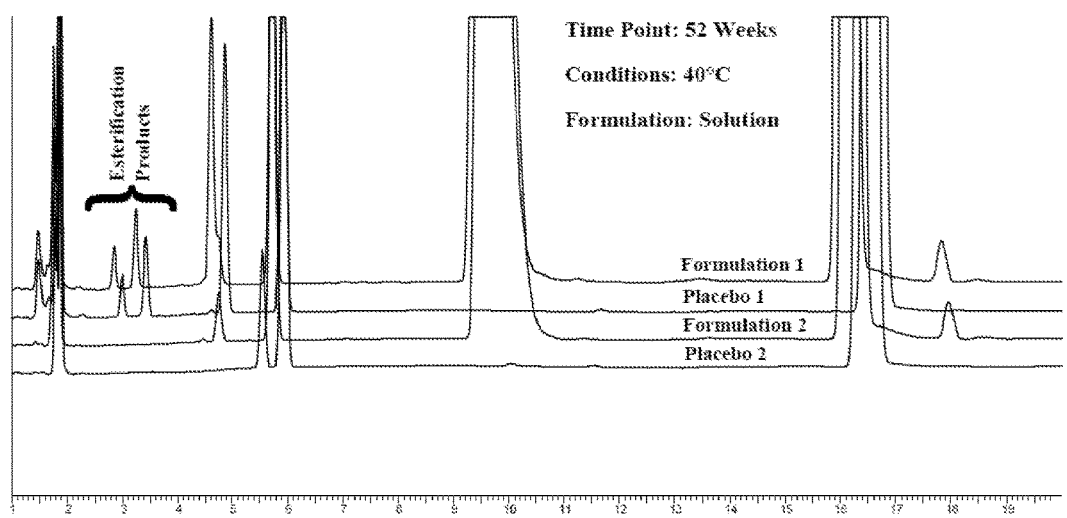
FIG. 2: Chromatograms showing esterification degradation peaks in formulation 1 (containing lisinopril, parabens and xylitol) and placebo 1 (containing parabens and xylitol) versus formulation 2 (containing lisinopril and paraben but no sugar alcohol) and placebo 2 (containing paraben but no sugar alcohol).

As shown in the examples and in FIG. 2, paraben preservatives (especially methylparaben) can react with selected sugars (glucose, fructose, sucrose, lactose, maltose) and sugar alcohols (xylitol, mannitol, lactitol, maltitol, sorbitol) to form transesterification reaction products. This can be undesirable from a formulation and stability standpoint as the transesterification creates additional degradants.

In some embodiments, the lisinopril oral liquid formulation described herein does not comprise a paraben preservative. In further embodiments, the lisinopril oral liquid formulation described herein does not comprise a paraben preservative when the formulation also comprises a sugar or sugar alcohol.

pH of Lisinopril Oral Liquid Formulations

Buffering agents maintain the pH of the lisinopril oral liquid formulation described herein. Non-limiting examples of buffering agents include, but are not limited to sodium bicarbonate, potassium bicarbonate, magnesium hydroxide, magnesium lactate, magnesium glucomate, aluminum hydroxide, aluminum hydroxide/sodium bicarbonate co-precipitate, mixture of an amino acid and a buffer, a mixture of aluminum glycinate and a buffer, a mixture of an acid salt of an amino acid and a buffer, and a mixture of an alkali salt of an amino acid and a buffer. Additional buffering agents include citric acid, sodium citrate, sodium tartrate, sodium acetate, sodium carbonate, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts. Some buffering agents also impart effervescent qualities when a powder is reconstituted in a solution.

In some embodiments, the lisinopril oral liquid formulation described herein comprises a buffer.

In some embodiments, the buffer in the lisinopril oral liquid formulation described herein comprises citric acid. In some embodiments, the buffer in the lisinopril oral liquid formulation described herein comprises citric acid and sodium citrate.

In some embodiments, the buffer in the lisinopril oral liquid formulation described herein comprises phosphoric acid. In some embodiments, the buffer in the lisinopril oral liquid formulation described herein comprises sodium phosphate.

In some embodiments, the buffer concentration is between about 5 mM and about 50 mM. In some embodiments, the buffer concentration is between about 5 mM and about 20 mM. In some embodiments, the buffer concentration is about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, or about 20 mM. In some embodiments, the buffer concentration is about 5 mM. In some embodiments, the buffer concentration is about 10 mM. In some embodiments, the buffer concentration is about 20 mM.

In some embodiments, modulation of the pH is desired to provide the lowest impurity profile. In the exemplary stability studies, the main lisinopril degradants are lisinopril diketopiperazine (also known as: Related Compound A) and lisinopril hydrolysate:

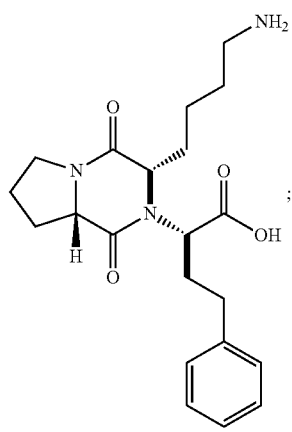

lisinopril diketopiperazine

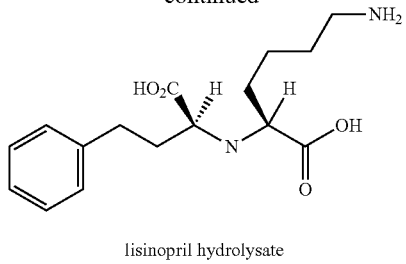

lisinopril hydrolysate

In some embodiments, the percentage of lisinopril diketopiperazine (Related Compound A) and lisinopril hydrolysate formation is increased when the pH is below 4. (See tables A-2, B-2, C-2, F-2, and FIG. 1).

In some embodiments, the pH of the lisinopril oral liquid formulation described herein is less than about 4. In some embodiments, the pH of the lisinopril oral liquid formulation described herein is more than about 5. In some embodiments, the pH of the lisinopril oral liquid formulation described herein is between about 4 and about 5. In some embodiments, the pH of the lisinopril oral liquid formulation described herein is about 4, about 4.1, about 4.2, about 4.3, about 4.4, about 4.5, about 4.6, about 4.7, about 4.8, about 4.9, or about 5. In some embodiments, the pH of the lisinopril oral liquid formulation described herein is between about 5 and about 8.

In some embodiments, citric acid is present in about 0.50 mg/ml to about 5.5 mg/ml in the oral liquid formulation. In other embodiments, citric acid is present in about 0.50 mg/ml to about 2 mg/mL in the oral liquid formulation. In other embodiments, citric acid is present in about 0.50 mg/ml, about 0.55 mg/ml, about 0.60 mg/ml, about 0.65 mg/ml, about 0.70 mg/ml, about 0.75 mg/ml, about 0.80 mg/ml, about 0.85 mg/ml, about 0.90 mg/ml, about 0.95 mg/ml, about 1.0 mg/ml, about 1.05 mg/ml, about 1.1 mg/ml, about 1.15 mg/ml, about 1.2 mg/ml, 1.25 mg/ml, about 1.30 mg/ml, about 1.35 mg/ml, about 1.4 mg/ml, about 1.45 mg/ml, about 1.5 mg/ml, about 1.55 mg/ml, about 1.6 mg/ml, about 1.65 mg/ml, about 1.7 mg/ml, about 1.75 mg/ml, about 1.80 mg/ml, about 1.85 mg/ml, about 1.9 mg/ml, about 1.95 mg/ml, or about 2 mg/ml in the oral liquid formulation. In some embodiments, citric acid is present in about 0.86 mg/ml in the oral liquid formulation. In some embodiments, citric acid is present in about 1.92 mg/ml in the oral liquid formulation. In some embodiments, citric acid is present in about 5.5 mg/ml in the oral liquid formulation.

In some embodiments, citric acid is present in about 0.1% w/w to about 5% w/w of the solids in the oral liquid formulation. In other embodiments, citric acid is present in about 0.10% w/w, about 0.15% w/w, about 0.20% w/w, about 0.25% w/w, about 0.30% w/w, about 0.35% w/w, about 0.40% w/w, about 0.45% w/w, about 0.50% w/w, about 0.55% w/w, about 0.60% w/w, about 0.65% w/w, about 0.70% w/w, about 0.75% w/w, about 0.80% w/w, about 0.85% w/w, about 0.90% w/w, about 0.95% w/w, about 1% w/w, about 1.5% w/w, about 2% w/w, about 2.5% w/w, about 3% w/w, about 3.5% w/w, about 4% w/w, about 4.5% w/w, or about 5% w/w of the solids in the oral liquid formulation. In some embodiments, citric acid is present in about 0.55% w/w the solids in the oral liquid formulation.

In some embodiments, citric acid is present in about 15% w/w to about 35% w/w of the powder formulation. In other embodiments, citric acid is present in about 15% w/w, about 15.5% w/w, about 16% w/w, about 16.5% w/w, about 17% w/w, about 17.5% w/w, about 18% w/w, about 18.5% w/w, about 19% w/w, about 19.5% w/w, about 20% w/w, about 20.5% w/w, about 21% w/w, about 21.5% w/w, about 22% w/w, about 22.5% w/w, about 23% w/w, about 23.5% w/w, about 24% w/w, about 24.5% w/w, about 25% w/w, about 25.5% w/w, about 26% w/w, about 26.5% w/w, about 27% w/w, about 27.5% w/w, about 28% w/w, about 28.5% w/w, about 29% w/w, about 29.5% w/w, about 30% w/w, about 30.5% w/w, about 31% w/w, about 31.5% w/w, about 32% w/w, about 32.5% w/w, about 33% w/w, about 33.5% w/w, about 34% w/w, about 34.5% w/w, or about 35% w/w of the solids in the oral liquid formulation. In some embodiments, citric acid is present in about 0.55% w/w the solids in the oral liquid formulation.

In some embodiments, sodium citrate is present in about 1.2 mg/ml to about 8.8 mg/ml in the oral liquid formulation. In other embodiments, sodium citrate is present in about 1.2 mg/ml to about 1.7 mg/mL in the oral liquid formulation. In other embodiments, sodium citrate is present in about 1.2 mg/ml, about 1.25 mg/ml, about 1.30 mg/ml, about 1.35 mg/ml, about 1.40 mg/ml, about 1.45 mg/ml, about 1.50 mg/ml, about 1.55 mg/ml, about 1.60 mg/ml, about 1.65 mg/ml, or about 1.7 mg/ml in the oral liquid formulation. In some embodiments, sodium citrate is present in about 1.44 mg/ml in the oral liquid formulation. In some embodiments, sodium citrate is present in about 8.8 mg/ml in the oral liquid formulation.

In some embodiments, sodium citrate is present in about 0.1% w/w to about 5% w/w of the solids in the oral liquid formulation. In other embodiments, citric acid is present in about 0.10% w/w, about 0.15% w/w, about 0.20% w/w, about 0.25% w/w, about 0.30% w/w, about 0.35% w/w, about 0.40% w/w, about 0.45% w/w, about 0.50% w/w, about 0.55% w/w, about 0.60% w/w, about 0.65% w/w, about 0.70% w/w, about 0.75% w/w, about 0.80% w/w, about 0.85% w/w, about 0.90% w/w, about 0.95% w/w, about 1% w/w, about 1.5% w/w, about 2% w/w, about 2.5% w/w, about 3% w/w, about 3.5% w/w, about 4% w/w, about 4.5% w/w, or about 5% w/w of the solids in the oral liquid formulation. In some embodiments, sodium citrate is present in about 0.93% w/w of the solids in the oral liquid formulation.

In other embodiments, sodium citrate is present in about 25% w/w to about 35% w/w of the solids in the oral liquid formulation. In other embodiments, citric acid is present in about 25% w/w, about 25.5% w/w, about 26% w/w, about 26.5% w/w, about 27% w/w, about 27.5% w/w, about 28% w/w, about 28.5% w/w, about 29% w/w, about 29.5% w/w, or about 30% w/w, about 30.5% w/w, about 31% w/w, about 31.5% w/w, about 32% w/w, about 32.5% w/w, about 33% w/w, about 33.5% w/w, about 34% w/w, about 34.5% w/w, or about 35% w/w of the solids in the oral liquid formulation. In some embodiments, sodium citrate is present in about 30% w/w of the solids in the oral liquid formulation.

In other embodiments, sodium citrate is not added to the formulation.

Additional Excipients

In further embodiments, the lisinopril oral liquid formulation described herein comprises additional excipients including, but not limited to, glidants, flavoring agents, coloring agents and thickeners. Additional excipients such as bulking agents, tonicity agents and chelating agents are within the scope of the embodiments.

Glidants are substances that improve flowability of a powder. Suitable glidants include, but are not limited to, calcium phosphate tribasic, calcium silicate, cellulose (powdered), colloidal silicon dioxide, magnesium silicate, magnesium trisilicate, silicon dioxide, starch, talc and the like. In some embodiments, the lisinopril powder formulations described herein comprise a glidant.

In another embodiment, the lisinopril oral liquid formulation described herein comprises a flavoring agent or flavorant to enhance the taste or aroma of the formulation in liquid form. Suitable natural or synthetic flavoring agents can be selected from standard reference books, for example Fenaroli's Handbook of Flavor Ingredients, 3rd edition (1995). Non-limiting examples of suitable natural flavors, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, *eucalyptus*, fennel, fig, ginger, grape, grapefruit, guava, hop, lemon, licorice, lime, malt, mandarin, molasses, nutmeg, mixed berry, orange, peach, pear, peppermint, pineapple, raspberry, rose, spearmint, strawberry, tangerine, tea, vanilla, wintergreen, etc. Also useful, particularly where the formulation is intended primarily for pediatric use, is tutti-frutti or bubblegum flavor, a compounded flavoring agent based on fruit flavors. Presently preferred flavoring agents include anise, cinnamon, cacao, orange, peppermint, cherry (in particular wild cherry), grape, bubblegum, vanilla, and mixed berry. Flavoring agents can be used singly or in combinations of two or more.

In further embodiments, the lisinopril oral liquid formulation described herein comprises a coloring agent for identity and/or aesthetic purposes. Suitable coloring agents illustratively include FD&C Red No. 3, FD&C Red No. 20, FD&C Red No. 40, FD&C Yellow No. 6, FD&C Blue No. 2, D&C Green No. 5, D&C Orange No. 5, caramel, ferric oxide and mixtures thereof.

In further embodiments, the lisinopril oral liquid formulation described herein comprises a thickener. Thickeners impart viscosity or weight to the resultant liquid forms from the lisinopril formulation described herein. Exemplary thickeners include dextrin, cellulose derivatives (ethylcellulose, hydroxyethyl cellulose, methylcellulose, hypromellose, and the like) starches, pectin, polyethylene glycol, polyethylene oxide, trehalose and certain gums (xanthan gum, locust bean gum, etc.). In certain embodiments, the lisinopril oral liquid formulations comprise a thickener.

Additional excipients are contemplated in the lisinopril oral liquid formulation embodiments. These additional excipients are selected based on function and compatibility with the lisinopril oral liquid formulations described herein and may be found, for example in *Remington: The Science and Practice of Pharmacy*, Nineteenth Ed (Easton, Pa.: Mack Publishing Company, 1995); Hoover, John E., *Remington's Pharmaceutical Sciences*, (Easton, Pa.: Mack Publishing Co 1975); Liberman, H. A. and Lachman, L., Eds., *Pharmaceutical Dosage Forms* (New York, N.Y.: Marcel Decker 1980); and *Pharmaceutical Dosage Forms and Drug Delivery Systems*, Seventh Ed (Lippincott Williams & Wilkins 1999), herein incorporated by reference in their entirety.

Preparation of Lisinopril Oral Liquid Formulation

Preparation of the lisinopril oral liquid formulation described herein includes any known pharmaceutical method. In one embodiment, the lisinopril oral liquid formulation described herein is prepared by dissolving the buffer, the preservative, lisinopril, and the sweetener in water and adjusting the pH as needed with sodium hydroxide or hydrochloric acid. In one embodiment, the oral lisinopril oral liquid formulation described herein is prepared by dissolving citric acid anhydrous, sodium citrate anhydrous, sodium benzoate, lisinopril dihydrate, and xylitol in water and adjusting the pH as needed with sodium hydroxide or hydrochloric acid. In some embodiments, the order of addition does not matter. In some embodiments, the lisinopril dissolves slightly slower if added after the xylitol. In some embodiments, the pH does not need to be adjusted with sodium hydroxide or hydrochloric acid.

Provided herein is a process for preparing a stable oral liquid formulation comprising lisinopril, xylitol, a buffer, and sodium benzoate, the process which comprises the step of adding about 0.86 mg/ml anhydrous citric acid, about 1.44 mg/ml anhydrous sodium citrate anhydrous, about 0.80 mg/ml sodium benzoate, about 1.09 mg/ml lisinopril dihydrate, and about 150 mg/ml xylitol to water; adjusting the volume to the desired volume by adding more water; and adjusting the pH to 4.9 by adding sodium hydroxide or hydrochloric acid.

Stability

The main lisinopril degradants are lisinopril diketopiperazine (also known as: Related Compound A) and lisinopril hydrolysate.

The lisinopril oral liquid formulations described herein are stable in various storage conditions including refrigerated, ambient and accelerated conditions. Stable as used herein refer to lisinopril oral liquid formulations having about 95% or greater of the initial lisinopril amount and about 5% w/w or less total impurities or related substances at the end of a given storage period. The percentage of impurities is calculated from the amount of impurities relative to the amount of lisinopril. Stability is assessed by HPLC or any other known testing method. In some embodiments, the stable lisinopril oral liquid formulations have about 5% w/w, about 4% w/w, about 3% w/w, about 2.5% w/w, about 2% w/w, about 1.5% w/w, about 1% w/w, or about 0.5% w/w total impurities or related substances. In other embodiments, the stable lisinopril oral liquid formulations have about 5% w/w total impurities or related substances. In yet other embodiments, the stable lisinopril oral liquid formulations have about 4% w/w total impurities or related substances. In yet other embodiments, the stable lisinopril oral liquid formulations have about 3% w/w total impurities or related substances. In yet other embodiments, the stable lisinopril oral liquid formulations have about 2% w/w total impurities or related substances. In yet other embodiments, the stable lisinopril oral liquid formulations have about 1% w/w total impurities or related substances.

At refrigerated and ambient conditions, the lisinopril oral liquid formulations described herein are stable for at least 1 month, at least 2 months, at least 3 months, at least 6 months, at least 9 months, at least 12 months, at least 15 months, at least 18 months, at least 24 months, at least 30 months and at least 36 months. At accelerated conditions, the lisinopril oral liquid formulations described herein are stable for at least 1 month, at least 2 months, at least 3 months, at least 4 months, at least 5 months, at least 6 months, at least 7 months, at least 8 months, at least 9 months, at least 10 months, at least 11 months or at least 12 months. Accelerated conditions include temperature and/or relative humidity (RH) that are above ambient levels (e.g. 25±5° C.; 55±10% RH). In some instances, an accelerated condition is at about 30° C., about 35° C., about 40° C., about 45° C., about 50° C., about 55° C. or about 60° C. In other instances, an accelerated condition is above 65% RH, about 70% RH, about 75% RH or about 80% RH. In further instances, an accelerated condition is about 40° C. or 60° C. at ambient humidity. In yet further instances, an accelerated condition is about 40° C. at 75±5% RH humidity.

Provided herein are various embodiments of lisinopril oral liquid formulations. In one aspect, the lisinopril oral liquid formulation comprises (i) lisinopril or a pharmaceutically acceptable salt or solvate thereof, (ii) a sweetener that is xylitol, (iii) a buffer comprising citric acid (iv) a preservative that is sodium benzoate, and (v) water; wherein the pH of the formulation is between about 4 and about 5; and wherein the formulation is stable at about 25±5° C. for at least 12 months. In some embodiments, the buffer further comprises sodium citrate.

In one aspect, the lisinopril oral liquid formulation comprises (i) about 1 mg/ml lisinopril or a pharmaceutically acceptable salt or solvate thereof, (ii) about 150 mg/ml of a sweetener that is xylitol, (iii) a buffer comprising about 0.86 mg/ml citric acid, (iv) about 0.8 mg/ml of a preservative that is sodium benzoate; and (v) water; wherein the pH of the formulation is between about 4 and about 5; and wherein the formulation is stable at about 25±5° C. for at least 12 months. In some embodiments, the buffer further comprises about 1.44 mg/ml sodium citrate.

In one aspect, the lisinopril oral liquid formulation comprises (i) lisinopril or a pharmaceutically acceptable salt or solvate thereof, (ii) a sweetener that is sucralose, (iii) a buffer comprising citric acid, (iv) a preservative that is sodium benzoate; and (v) water wherein the formulation is stable at about 25±5° C. for at least 12 months.

In one aspect, the lisinopril oral liquid formulation comprises (i) about 1 mg/ml lisinopril or a pharmaceutically acceptable salt or solvate thereof, (ii) about 2 mg/ml of a sweetener that is sucralose, (iii) a buffer comprising about 1.92 mg/ml citric acid, (iv) about 0.8 mg/ml of a preservative that is sodium benzoate; and (v) water wherein the formulation is stable at about 25±5° C. for at least 12 months.

In one aspect, the lisinopril oral liquid formulation comprises (i) about 1 mg/ml lisinopril or a pharmaceutically acceptable salt or solvate thereof, (ii) about 0.7 mg/ml of a sweetener that is sucralose, (iii) a buffer comprising about 1.92 mg/ml citric acid, (iv) about 0.8 mg/ml of a preservative that is sodium benzoate; and (v) water wherein the formulation is stable at about 25±5° C. for at least 12 months.

In one aspect, the lisinopril oral liquid formulation comprises (i) lisinopril or a pharmaceutically acceptable salt or solvate thereof, (ii) of a sweetener that is sucralose, (iii) a buffer comprising citric acid, (iv) a preservative that is methyl paraben, (v) a preservative that is propylparaben, and (vi) water; wherein the formulation is stable at about 25±5° C. for at least 12 months.

In one aspect, the lisinopril oral liquid formulation comprises (i) about 1 mg/ml lisinopril or a pharmaceutically acceptable salt or solvate thereof, (ii) about 2 mg/ml of a sweetener that is sucralose, (iii) a buffer comprising about 1.92 mg/ml citric acid, (iv) about 1.72 mg/ml of a preservative that is methyl paraben sodium, (v) about 0.17 mg/mL of a preservative that is propylparaben sodium, and (vi) water; wherein the formulation is stable at about 25±5° C. for at least 12 months.

In one aspect, the lisinopril oral liquid formulation comprises (i) lisinopril or a pharmaceutically acceptable salt or solvate thereof, (ii) a sweetener that is xylitol, (iii) a buffer comprising citric acid, (iv) a preservative that is sodium benzoate; and (v) water; wherein the formulation is stable at about 25±5° C. for at least 12 months.

In one aspect, the lisinopril oral liquid formulation comprises (i) about 1 mg/ml lisinopril or a pharmaceutically acceptable salt or solvate thereof, (ii) about 150 mg/ml of a sweetener that is xylitol, (iii) a buffer comprising about 1.92 mg/ml citric acid, (iv) about 0.8 mg/ml of a preservative that is sodium benzoate; and (v) water; wherein the formulation is stable at about 25±5° C. for at least 12 months.

In one aspect, the lisinopril oral liquid formulation, comprises (i) lisinopril or a pharmaceutically acceptable salt or solvate thereof, (ii) a sweetener that is xylitol, (iii) a buffer comprising citric acid, (iv) a preservative that is methyl paraben, (v) a preservative that is propylparaben; and (vi) water; wherein the formulation is stable at about 25±5° C. for at least 12 months.

In one aspect, the lisinopril oral liquid formulation comprises (i) about 1 mg/ml lisinopril or a pharmaceutically acceptable salt or solvate thereof, (ii) about 150 mg/ml of a sweetener that is xylitol, (iii) a buffer comprising about 1.92 mg/ml citric acid, (iv) about 1.72 mg/ml of a preservative that is methyl paraben sodium, (v) about 0.17 mg/mL of a preservative that is propylparaben sodium; and (vi) water; wherein the formulation is stable at about 25±5° C. for at least 12 months.

In one aspect, the lisinopril oral liquid formulation comprises (i) lisinopril or a pharmaceutically acceptable salt or solvate thereof, (ii) a sweetener that is xylitol, (iii) a second sweetener that is sucralose (iv) a buffer comprising citric acid, (v) a preservative that is methyl paraben, (vi) a preservative that is propylparaben; and (vii) water; wherein the formulation is stable at about 25±5° C. for at least 12 months.

In one aspect, the lisinopril oral liquid formulation comprises (i) about 1 mg/ml lisinopril or a pharmaceutically acceptable salt or solvate thereof, (ii) about 100 mg/ml of a sweetener that is xylitol, (iii) about 2 mg/ml of a second sweetener that is sucralose (iv) a buffer comprising about 1.92 mg/ml citric acid, (v) about 1.72 mg/ml of a preservative that is methyl paraben sodium, (vi) about 0.17 mg/mL of a preservative that is propylparaben sodium; and (vii) water; wherein the formulation is stable at about 25±5° C. for at least 12 months.

In one aspect, the lisinopril oral liquid formulation comprises (i) lisinopril or a pharmaceutically acceptable salt or solvate thereof, (ii) a sweetener that is sucralose, (iii) a buffer comprising sodium phosphate, (iv) a preservative that is methyl paraben, (v) a preservative that is propylparaben, and (vi) water; wherein the formulation is stable at about 25±5° C. for at least 12 months.

In one aspect, the lisinopril oral liquid formulation comprises (i) about 1 mg/ml lisinopril or a pharmaceutically acceptable salt or solvate thereof, (ii) about 0.7 mg/ml of a sweetener that is sucralose, (iii) a buffer comprising about 2.4 mg/ml monobasic sodium phosphate, (iv) about 1.72 mg/ml of a preservative that is methyl paraben sodium, (v) about 0.225 mg/mL of a preservative that is propylparaben sodium, and (vi) water; wherein the formulation is stable at about 25±5° C. for at least 12 months.

Lisinopril Powder Formulations

In another aspect, lisinopril oral liquid formulations described herein are prepared from the reconstitution of a lisinopril powder formulation. In some embodiments, the lisinopril powder formulation comprising lisinopril, a sweetener, a preservative, and optionally an excipient is dissolved in water, a buffer, other aqueous solvent, or a liquid to form a lisinopril oral liquid formulation. In one embodiment, the sweetening agent is xylitol. In one embodiment, the sweetener is mannitol. In one embodiment, the sweetening agent is sucralose. In another embodiment, the preservative is sodium benzoate. In one embodiment, the preservative is a paraben preservative. In one aspect, the lisinopril powder formulation described herein comprises lisinopril, xylitol, and sodium benzoate. In some embodiments, the lisinopril powder formulation herein further comprises a flavoring agent. In some embodiments, the lisinopril powder formulation herein further comprises one or more buffering agents.

In some embodiments, lisinopril is present in about 0.5% w/w to about 5% w/w of the powder formulation. In other embodiments, Lisinopril is present in about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, or about 5% w/w of the powder formulation. In some embodiments, lisinopril is present in about 0.5% w/w to about 1% w/w of the powder formulation. In some embodiments, lisinopril is present in about 0.6% w/w to about 0.8% w/w of the powder formulation. In some embodiments, lisinopril is present in about 0.7% w/w of the powder formulation.

In some embodiments, lisinopril is present in about 10% w/w to about 20% w/w of the powder formulation. In other embodiments, lisinopril is present in about 10% w/w, about 10.5% w/w, about 11% w/w, about 11.5% w/w, about 12% w/w, about 12.5% w/w, about 13% w/w, about 13.5% w/w, about 14% w/w, about 14.5% w/w, about 15% w/w, about 15.5% w/w, about 16% w/w, about 16.5% w/w, about 17% w/w, about 17.5% w/w, about 18% w/w, about 18.5% w/w, about 19% w/w, about 19.5% w/w, or about 20% w/w of the powder formulation. In some embodiments, lisinopril is present in about 14% w/w to about 16% w/w of the powder formulation. In some embodiments, lisinopril is present in about 17% w/w to about 19% w/w of the powder formulation.

Various amounts and concentrations of other components (sweeteners, buffers, preservatives, and the like) in the lisinopril powder formulations are found in the previous section describing the amounts and concentrations for the analogous lisinopril oral liquid formulations. For example, in some embodiments where sucralose is present in about 20% w/w to about 40% w/w of the solids in the oral liquid formulation; in an analogous lisinopril powder formulation, sucralose would be about 20% w/w to about 40% w/w in the powder formulation. In some embodiments where sodium benzoate is present in about 10% w/w to about 15% w/w of the solids in the oral liquid formulation, in an analogous lisinopril powder formulation sodium benzoate is present in about 10% w/w to about 15% w/w in the powder formulation.

Liquid vehicles suitable for the lisinopril powder formulations to be reconstituted into an oral solution described herein are selected for a particular oral liquid formulation (solution, suspension, etc.) as well as other qualities such as clarity, toxicity, viscosity, compatibility with excipients, chemical inertness, palatability, odor, color and economy.

Exemplary liquid vehicles include water, ethyl alcohol, glycerin, propylene glycol, syrup (sugar or other sweetener based, e.g., Ora-Sweet® SF sugar-free flavored syrup), juices (apple, grape, orange, cranberry, cherry, tomato and the like), other beverages (tea, coffee, soft drinks, milk and the like), oils (olive, soybean, corn, mineral, castor and the like), and combinations or mixtures thereof. Certain liquid vehicles, e.g., oil and water, can be combined together to form emulsions. In some embodiments, water is used for as a vehicle for a lisinopril oral liquid formulation. In other embodiments, a syrup is used for as a vehicle for a lisinopril oral liquid formulation. In yet other embodiments, a juice is used for as a vehicle for a lisinopril oral liquid formulation.

Buffering agents maintain the pH of the liquid lisinopril formulation. Non-limiting examples of buffering agents include, but are not limited to sodium bicarbonate, potassium bicarbonate, magnesium hydroxide, magnesium lactate, magnesium gluconate, aluminum hydroxide, aluminum hydroxide/sodium bicarbonate co precipitate, mixture of an amino acid and a buffer, a mixture of aluminum glycinate and a buffer, a mixture of an acid salt of an amino acid and a buffer, and a mixture of an alkali salt of an amino acid and a buffer. Additional buffering agents include citric acid, sodium citrate, sodium tartarate, sodium acetate, sodium carbonate, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts. Some buffering agents also impart effervescent qualities when a powder is reconstituted in a solution.

In some embodiments, the reconstituted oral liquid formulation comprises a buffer. In some embodiments, the buffer comprises citric acid and sodium citrate. In further embodiments, the lisinopril powder formulation described herein comprises additional excipients including, but not limited to, glidants, flavoring agents, coloring agents and thickeners. Additional excipients such as bulking agents, tonicity agents and chelating agents are within the scope of the embodiments.

Glidants are substances that improve flowability of a powder. Suitable glidants include, but are not limited to, calcium phosphate tribasic, calcium silicate, cellulose (powdered), colloidal silicon dioxide, magnesium silicate, magnesium trisilicate, silicon dioxide, starch, talc and the like. In some embodiments, the lisinopril powder formulations described herein comprise a glidant.

In another embodiment, the lisinopril powder formulation described herein comprises a flavoring agent or flavorant to enhance the taste or aroma of the formulation in liquid form. Suitable natural or synthetic flavoring agents can be selected from standard reference books, for example Fenaroli's Handbook of Flavor Ingredients, 3rd edition (1995). Non-limiting examples of suitable natural flavors, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, *eucalyptus*, fennel, fig, ginger, grape, grapefruit, guava, hop, lemon, licorice, lime, malt, mandarin, molasses, nutmeg, mixed berry, orange, peach, pear, peppermint, pineapple, raspberry, rose, spearmint, strawberry, tangerine, tea, vanilla, wintergreen, etc. Also useful, particularly where the formulation is intended primarily for pediatric use, is tutti-frutti or bubblegum flavor, a compounded flavoring agent based on fruit flavors. Presently preferred flavoring agents include anise, cinnamon, cacao, orange, peppermint, cherry (in particular wild cherry), grape, bubblegum, vanilla, and mixed berry. Flavoring agents can be used singly or in combinations of two or more.

In further embodiments, the lisinopril powder formulation described herein comprises a coloring agent for identity and/or aesthetic purposes. Suitable coloring agents illustratively include FD&C Red No. 3, FD&C Red No. 20, FD&C Red No. 40, FD&C Yellow No. 6, FD&C Blue No. 2, D&C Green No. 5, D&C Orange No. 5, caramel, ferric oxide and mixtures thereof.

In further embodiments, the lisinopril powder formulation described herein comprises a thickener. Thickeners impart viscosity or weight to the resultant liquid forms from the lisinopril formulation described herein. Exemplary thickeners include dextrin, cellulose derivatives (ethylcellulose, hydroxyethyl cellulose, methylcellulose, hypromellose, and the like) starches, pectin, polyethylene glycol, polyethylene oxide, trehalose and certain gums (xanthan gum, locust bean gum, etc.).

Additional excipients are contemplated in the lisinopril powder formulation embodiments. These additional excipients are selected based on function and compatibility with the lisinopril powder formulation described herein and may be found, for example in *Remington: The Science and Practice of Pharmacy*, Nineteeth Ed (Easton, Pa.: Mack Publishing Company, 1995); Hoover, John E., *Remington's Pharmaceutical Sciences*, (Easton, Pa.: Mack Publishing Co 1975); Liberman, H. A. and Lachman, L., Eds., *Pharmaceutical Dosage Forms* (New York, N.Y.: Marcel Decker 1980); and *Pharmaceutical Dosage Forms and Drug Delivery Systems*, Seventh Ed (Lippincott Williams & Wilkins 1999), herein incorporated by reference in their entirety.

In some embodiments, the lisinopril oral liquid formulation prepared from the powder formulations described herein are homogenous. Homogenous liquids as used herein refer to those liquids that are uniform in appearance, identity, consistency and drug concentration per volume. Non-homogenous liquids include such liquids that have varied coloring, viscosity and/or aggregation of solid particulates, as well as non-uniform drug concentration in a given unit volume. Homogeneity in liquids are assessed by qualitative identification or appearance tests and/or quantitative HPLC testing or the like. The mixing methods and excipients described herein are selected to impart a homogenous quality to a resultant lisinopril oral liquid formulation.

Mixing methods encompass any type of mixing that result in a homogenous lisinopril oral liquid formulation. In some embodiments, a quantity of a lisinopril powder formulation is added to a liquid vehicle and then mixed by a stirring, shaking, swirling, agitation element or a combination thereof. In certain instances, a fraction of a lisinopril powder formulation (i.e., one-half, one-third, one-fourth, etc.) is added to a liquid vehicle, mixed by stirring, shaking, swirling, agitation or a combination thereof, and the subsequent powder fraction(s) is added and mixed. In other embodiments, a liquid vehicle is added to a lisinopril powder formulation in a container, for example, a bottle, vial, bag, beaker, syringe, or the like. The container is then mixed by stirring, shaking, swirling, agitation, inversion or a combination thereof. In certain instances, a fractional volume of the liquid vehicle (i.e., one-half, one-third, one-fourth volume, etc.) is added to a lisinopril powder formulation in a container, mixed by stirring, shaking, swirling, agitation, inversion or a combination thereof; and the subsequent liquid fraction(s) is added and mixed. In certain instances, a one-half fractional volume of the liquid vehicle is added to a lisinopril powder formulation in a container and mixing by shaking; the other one-half fractional volume of the liquid vehicle is then subsequently added and mixed. In any of the above embodiments, mixing (i.e., stirring, shaking, swirling, agitation, inversion or a combination thereof) occurs for a certain time intervals such as about 10 seconds, about 20 seconds, about 30 seconds, about 45 seconds, about 60 seconds, about 90 seconds, about 120 seconds, about 2.5 minutes, about 3 minutes, about 3.5 minutes, about 4 minutes, or about 5 minutes. In embodiments, where there are two or more mixing steps, the time intervals for each mixing can be the same (e.g., 2×10 seconds) or different (e.g., 10 seconds for first mixing and 20 seconds for second mixing) In any of the above embodiments, a lisinopril oral liquid formulation is allowed to stand for a period of time such as about 10 minutes, about 20 minutes, about 30 minutes, about 45 minutes, about 1 hour, about 1.5 hours or about 2 hours, to allow any air bubbles resultant from any of the mixing methods to dissipate.

Stability of Lisinopril Powder Formulations

The lisinopril powder formulations described herein are stable in various storage conditions including refrigerated, ambient and accelerated conditions. Stable as used herein refer to lisinopril powder formulations having about 95% or greater of the initial lisinopril amount and 5% w/w or less total impurities or related substances at the end of a given storage period. The percentage of impurities is calculated from the amount of impurities relative to the amount of lisinopril. Stability is assessed by HPLC or any other known testing method. In some embodiments, the stable lisinopril powder formulations have about 5% w/w, about 4% w/w, about 3% w/w, about 2.5% w/w, about 2% w/w, about 1.5% w/w, about 1% w/w, or about 0.5% w/w total impurities or related substances. In other embodiments, the stable lisinopril powder formulations have about 5% w/w total impurities or related substances. In yet other embodiments, the stable lisinopril powder formulations have about 4% w/w total impurities or related substances. In yet other embodiments, the stable lisinopril powder formulations have about 3% w/w total impurities or related substances. In yet other embodiments, the stable lisinopril powder formulations have about 2% w/w total impurities or related substances. In yet other embodiments, the stable lisinopril powder formulations have about 1% w/w total impurities or related substances.

At refrigerated and ambient conditions, in some embodiments, the lisinopril powder formulations described herein are stable for at least 1 week, 2 weeks, 4 weeks, 6 weeks, 8 weeks, 10 weeks, 12 weeks, 16 weeks, 20 weeks, at least 24 weeks, at least 30 weeks, or at least 36 weeks. At accelerated conditions, in some embodiments, the lisinopril powder formulations described herein are stable for at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks or at least 12 weeks. Accelerated conditions include temperature and/or relative humidity (RH) that are above ambient levels (e.g. 25±4° C.; 55±10% RH). In some instances, an accelerated condition is at about 30° C., about 35° C., about 40° C., about 45° C., about 50° C., about 55° C. or about 60° C. In other instances, an accelerated condition is above 65% RH, about 70% RH, about 75% RH or about 80% RH. In further instances, an accelerated condition is about 40° C. or 60° C. at ambient humidity. In yet further instances, an accelerated condition is about 40° C. at 75±5% RH humidity.

Kits and Articles of Manufacture

For the lisinopril powder and liquid formulations described herein, kits and articles of manufacture are also described. Such kits can comprise a carrier, package, or container that is compartmentalized to receive one or more containers such as vials, tubes, and the like, each of the container(s) comprising one of the separate elements to be used in a method described herein including a lisinopril powder or liquid formulation. Suitable containers include, for example, bottles, vials, syringes, and test tubes. The containers can be formed from a variety of materials such as glass or plastic.

A kit will typically may comprise one or more additional containers, each with one or more of various materials (such as reagents, optionally in concentrated form, and/or devices) desirable from a commercial and user standpoint for a lisinopril powder or liquid formulation described herein. Non-limiting examples of such materials include, but not limited to, buffers, diluents, filters, needles, syringes, syringe adapter, carrier, package, container, vial and/or tube labels listing contents and/or instructions for use, and package inserts with instructions for use associated with a lisinopril powder or liquid formulation. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

Methods

Provided herein, in one aspect, are methods of treatment comprising administration of the lisinopril oral liquid formulations described herein to a subject. In some embodiments, the lisinopril oral liquid formulations described herein treat hypertension in a subject. Hypertension as used herein includes both primary (essential) hypertension or secondary hypertension. In certain instances, hypertension is classified in cases when blood pressure values are greater than or equal to 140/90 (systolic/diastolic) mm Hg in a subject. In certain instances, the lisinopril oral liquid formulations described herein treat a subject having a blood pressure value greater than or equal to 140/90 mm Hg. In certain instances, the lisinopril oral liquid formulations described herein treat primary (essential) hypertension in a subject. In other instances, the lisinopril oral liquid formulations described herein treat secondary hypertension in a subject.

In other embodiments, the lisinopril oral liquid formulations described herein treat prehypertension in a subject. Prehypertension as used herein refers to cases where a subject's blood pressure is elevated above normal but not to the level considered to be hypertension. In some instances, prehypertension is classified in cases when blood pressure values are 120-139/80-89 mm Hg. In certain instances, the lisinopril oral liquid formulations described herein treat a subject having a blood pressure value of 120-139/80-89 mm Hg.

In yet other embodiments, the lisinopril oral liquid formulations described herein are prophylactically administered to subjects suspected of having, predisposed to, or at risk of developing hypertension. In some embodiments, the administration of lisinopril oral liquid formulations described herein allow for early intervention prior to onset of hypertension. In certain embodiments, upon detection of a biomarker, environmental, genetic factor, or other marker, the lisinopril oral liquid formulations described herein are prophylactically administered to subjects.

In further embodiments, the lisinopril oral liquid formulations described herein treat heart failure (e.g., symptomatic congestive), asymptomatic left ventricular dysfunction, myocardial infarction, diabetic nephropathy and chronic renal failure. In certain instances, the lisinopril oral liquid formulations described herein is indicated as adjunctive therapy in the management of heart failure in patients who are not responding adequately to diuretics and *digitalis*. In certain instances, the lisinopril oral liquid formulations described herein treat symptomatic congestive heart failure. In other instances, the lisinopril oral liquid formulations described herein treat asymptomatic left ventricular dysfunction. In further instances, the lisinopril oral liquid formulations described herein treat myocardial infarction. In further instances, the lisinopril oral liquid formulations described herein treat hemodynamically stable patients within 24 h of acute myocardial infarction. In yet further instances, the lisinopril oral liquid formulations described herein treat diabetic nephropathy. In yet further instances, the lisinopril oral liquid formulations described herein treat chronic renal failure. In yet further instances, the lisinopril oral liquid formulations described herein is used in preventing renal and retinal complications of diabetes.

Dosing

In one aspect, the lisinopril oral liquid formulations are used for the treatment of diseases and conditions described herein. In addition, a method for treating any of the diseases or conditions described herein in a subject in need of such treatment, involves administration of lisinopril oral liquid formulations in therapeutically effective amounts to said subject.

Dosages of lisinopril oral liquid formulations described can be determined by any suitable method. Maximum tolerated doses (MTD) and maximum response doses (MRD) for lisinopril can be determined via established animal and human experimental protocols as well as in the examples described herein. For example, toxicity and therapeutic efficacy of lisinopril can be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Lisinopril dosages exhibiting high therapeutic indices are of interest. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized. Additional relative dosages, represented as a percent of maximal response or of maximum tolerated dose, are readily obtained via the protocols.

In some embodiments, the amount of a given lisinopril oral liquid formulation that corresponds to such an amount varies depending upon factors such as the particular lisinopril salt or solvate, disease condition and its severity, the identity (e.g., weight, sex) of the subject or host in need of treatment, but can nevertheless be determined according to the particular circumstances surrounding the case, including, e.g., the specific agent being administered, the liquid formulation type, the condition being treated, and the subject or host being treated.

In some embodiments, the lisinopril oral liquid formulations described herein are provided in a dose per day from about 0.01 mg to 100 mg, from about 0.1 mg to about 80 mg, from about 1 to about 60, from about 2 mg to about 40 mg of lisinopril. In certain embodiments, the lisinopril oral liquid formulations described herein are provided in a daily dose of about 0.01 mg, about 0.05 mg, about 0.1 mg, about 0.2 mg, about 0.4 mg, about 0.6 mg, about 0.8 mg, about 1 mg, about 1.5 mg, about 2 mg, about 2.5 mg, about 3 mg, about 4 mg, about 5 mg, about 6 mg, about 7 mg, about 8 mg, about 9 mg, about 10 mg, about 11 mg, about 12 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 76, mg, about 80 mg, about 85 mg, about 90 mg or about 100 mg, or any range derivable therein. In certain instances, the lisinopril oral liquid formulations described herein are provided in a dose per day of about 1 mg. In certain instances, the lisinopril oral liquid formulations described herein are provided in a dose per day of about 2 mg. In certain instances, the lisinopril oral liquid formulations described herein are provided in a dose per day of about 3 mg. In certain instances, the lisinopril oral liquid formulations described herein are provided in a dose per day of about 4 mg. In certain instances, the lisinopril oral liquid formulations described herein are provided in a dose per day of about 5 mg. In certain instances, the lisinopril oral liquid formulations described herein are provided in a dose per day of about 6 mg. In certain instances, the lisinopril oral liquid formulations described herein are provided in a dose per day of about 7 mg. In certain instances, the lisinopril oral liquid formulations described herein are provided in a dose per day of about 8 mg. In certain instances, the lisinopril oral liquid formulations described herein are provided in a dose per day of about 9 mg. In certain instances, the lisinopril oral liquid formulations described herein are provided in a dose per day of about 10 mg. In certain instances, the lisinopril oral liquid formulations described herein are provided in a dose per day of about 11 mg. In certain instances, the lisinopril oral liquid formulations described herein are provided in a dose per day of about 12 mg. The dose per day described herein can be given once per day or multiple times per day in the form of sub-doses given b.i.d., t.i.d., q.i.d., or the like where the number of sub-doses equal the dose per day.

In further embodiments, the daily dosages appropriate for the lisinopril oral liquid formulations described herein are from about 0.01 to about 1.0 mg/kg per body weight. In one embodiment, the daily dosages appropriate for the lisinopril oral liquid formulations are from about 0.02 to about 0.8 mg/kg lisinopril per body weight. In another embodiment, the daily dosage appropriate for the lisinopril oral liquid formulations are from about 0.05 to about 0.6 mg/kg per body weight. In another embodiment, the daily dosage appropriate for the lisinopril oral liquid formulations is about 0.05 mg/kg, about 0.06 mg/kg, about 0.07 mg/kg, about 0.08 mg/kg, about 0.10 mg/kg, about 0.15 mg/kg, about 0.20 mg/kg, about 0.25 mg/kg, about 0.30 mg/kg, about 0.40 mg/kg, about 0.50 mg/kg, about 0.60 mg/kg, about 0.61 mg/kg, about 0.62 mg/kg, about 0.63 mg/kg, about 0.64 mg/kg, or about 0.65 mg/kg.

In other embodiments the lisinopril oral liquid formulations are provided at the maximum tolerated dose (MTD) for lisinopril. In other embodiments, the amount of the lisinopril oral liquid formulations administered is from about 10% to about 90% of the maximum tolerated dose (MTD), from about 25% to about 75% of the MTD, or about 50% of the MTD. In particular embodiments, the amount of the lisinopril oral liquid formulations administered is from about 5%, 10%, 15%, 20%, 25%, 30%, 35%, 40%, 45%, 50%, 55%, 60%, 65%, 70%, 75%, 80%, 85%, 90%, 95%, 99%, or higher, or any range derivable therein, of the MTD for lisinopril.

In further embodiments, the lisinopril oral liquid formulations are provided in a dosage that is similar, comparable or equivalent to a dosage of a known lisinopril tablet formulation. In other embodiments, the lisinopril oral liquid formulations are provided in a dosage that provides similar, comparable or equivalent pharmacokinetic parameters (e.g., AUC, $C_{max}$, $T_{max}$, $C_{min}$, $T_{1/2}$) as a dosage of a known lisinopril tablet formulation. Similar, comparable or equivalent pharmacokinetic parameters, in some instances, refer to within 80% to 125%, 80% to 120%, 85% to 125%, 90% to 110%, or increments therein, of the given values. It should be recognized that the ranges can, but need not be symmetrical, e.g., 85% to 105%.

Administration

Administration of a lisinopril oral liquid formulation is at a dosage described herein or at other dose levels and formulations determined and contemplated by a medical practitioner. In certain embodiments, the lisinopril oral liquid formulations described herein are administered for prophylactic and/or therapeutic treatments. In certain therapeutic applications, the lisinopril oral liquid formulations are administered to a patient already suffering from a disease, e.g., hypertension, in an amount sufficient to cure the disease or at least partially arrest or ameliorate the symptoms, e.g., lower blood pressure. Amounts effective for this use depend on the severity of the disease, previous therapy, the patient's health status, weight, and response to the lisinopril formulations, and the judgment of the treating physician. Therapeutically effective amounts are optionally determined by methods including, but not limited to, a dose escalation clinical trial.

In prophylactic applications, the lisinopril oral liquid formulations described herein are administered to a patient susceptible to or otherwise at risk of a particular disease, e.g., hypertension. Such an amount is defined to be a "prophylactically effective amount or dose." In this use, the precise amounts also depend on the patient's state of health, weight, and the like. When used in a patient, effective amounts for this use will depend on the risk or susceptibility of developing the particular disease, previous therapy, the patient's health status and response to the lisinopril formulations, and the judgment of the treating physician.

In certain embodiments wherein the patient's condition does not improve, upon the doctor's discretion the administration of a lisinopril oral liquid formulation described herein are administered chronically, that is, for an extended period of time, including throughout the duration of the patient's life in order to ameliorate or otherwise control or limit the symptoms of the patient's disease. In other embodiments, administration of a lisinopril oral liquid formulation continues until complete or partial response of a disease.

In certain embodiments wherein a patient's status does improve, the dose of a lisinopril oral liquid formulation being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In some embodiments, lisinopril oral liquid formulations described herein are administered chronically. For example, in some embodiments, a lisinopril oral liquid formulation is administered as a continuous dose, i.e., administered daily to a subject. In some other embodiments, lisinopril oral liquid formulations described herein are administered intermittently (e.g. drug holiday that includes a period of time in which the formulation is not administered or is administered in a reduced amount).

In some embodiments a lisinopril oral liquid formulation is administered to a subject who is in a fasted state. A fasted state refers to a subject who has gone without food or fasted for a certain period of time. General fasting periods include at least 4 hours, at least 6 hours, at least 8 hours, at least 10 hours, at least 12 hours, at least 14 hours and at least 16 hours without food. In some embodiments, a lisinopril oral liquid formulation is administered orally to a subject who is in a fasted state for at least 8 hours. In other embodiments, a lisinopril oral liquid formulation is administered to a subject who is in a fasted state for at least 10 hours. In yet other embodiments, a lisinopril oral liquid formulation is administered to a subject who is in a fasted state for at least 12 hours. In other embodiments, a lisinopril oral liquid formulation is administered to a subject who has fasted overnight.

In other embodiments a lisinopril oral liquid formulation is administered to a subject who is in a fed state. A fed state refers to a subject who has taken food or has had a meal. In certain embodiments, a lisinopril oral liquid formulation is administered to a subject in a fed state 5 minutes post-meal, 10 minutes post-meal, 15 minutes post-meal, 20 minutes post-meal, 30 minutes post-meal, 40 minutes post-meal, 50 minutes post-meal, 1 hour post-meal, or 2 hours post-meal. In certain instances, a lisinopril oral liquid formulation is administered to a subject in a fed state 30 minutes post-meal. In other instances, a lisinopril oral liquid formulation is administered to a subject in a fed state 1 hour post-meal. In yet further embodiments, a lisinopril oral liquid formulation is administered to a subject with food.

In further embodiments described herein, a lisinopril oral liquid formulation is administered at a certain time of day for the entire administration period. For example, a lisinopril oral liquid formulation can be administered at a certain time in the morning, in the evening, or prior to bed. In certain instances, a lisinopril oral liquid formulation is administered in the morning. In other embodiments, a lisinopril oral liquid formulation can be administered at different times of the day for the entire administration period. For example, a lisinopril oral liquid formulation can be administered on 8:00 am in the morning for the first day, 12 pm noon for the next day or administration, 4 pm in the afternoon for the third day or administration, and so on.

Further Combinations

The treatment of certain diseases or conditions (e.g., hypertension, heart failure, myocardial infarction and the like) in a subject with a lisinopril oral liquid formulation described herein encompass additional therapies and treatment regimens with other agents in some embodiments. Such additional therapies and treatment regimens can include another therapy, e.g., additional anti-hypertensives, for treatment of the particular disease or condition in some embodiments. Alternatively, in other embodiments, additional therapies and treatment regimens include other agents used to treat adjunct conditions associated with the disease or condition or a side effect from the lisinopril oral liquid formulation in the therapy.

Additional agents for use in combination with a lisinopril oral liquid formulation described herein include, but are not limited to, diuretics (loop, thiazide, potassium-sparing, and the like), beta blockers (metoprolol, propanolol, pronethalol, and the like), alpha blockers (phentolamine, phenoxybenzamine, tamsulosin, prazosin, and the like), mixed alpha and beta blockers (bucindolol, carvedilol, labetalol), calcium channel blockers (dihydropyridines such as nifedipine, amlodipine, etc., dilitazem, verapamil and the like), angiotensin II receptor antagonists (saralasin, losartan, eprosartin, irbesartan, valsartan, and the like), other ACE inhibitors (captopril, quinapril, ramipril, enalapril, zofenopril, and the like), aldosterone antagonists (eplerenone, spironolactone and the like), vasodilators (hydralazine and the like) and alpha-2 agonists (clonidine, moxonidine, guanabenz and the like).

Certain Definitions

Unless defined otherwise, all technical and scientific terms used herein have the same meanings as commonly understood by one of ordinary skill in the art. Although any methods and materials similar or equivalent to those described herein can be used in the practice or testing of embodiments described herein, certain preferred methods, devices, and materials are now described.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent such as lisinopril is directed to the treatment and/or the amelioration of, reversal of, or stabilization of the symptoms of hypertension described herein.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with a lisinopril formulation, can include, but is not limited to, providing a lisinopril formulation into or onto the target tissue; providing a lisinopril formulation systemically to a patient by, e.g., oral administration whereby the therapeutic reaches the target tissue or cells. "Administering" a formulation may be accomplished by injection, topical administration, and oral administration or by other methods alone or in combination with other known techniques.

The term "animal" as used herein includes, but is not limited to, humans and non-human vertebrates such as wild, domestic and farm animals. As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is child. In further instances, the human is 12 years of age or younger. In certain instances, the human is elderly. In other instances, the human is 60 years of age or older. Other examples of subjects include experimental animals such as mice, rats, dogs, cats, goats, sheep, pigs, and cows. The experimental animal can be an animal model for a disorder, e.g., a transgenic mouse with hypertensive pathology. A patient can be a human suffering from hypertension, or its variants or etiological forms.

By "pharmaceutically acceptable", it is meant the carrier, diluent or excipient must be compatible with the other ingredients of the formulation and not deleterious to the recipient thereof.

The term "pharmaceutical formulation" shall mean a formulation comprising at least one active ingredient, whereby the formulation is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology). As such, a non-limiting example of a "therapeutically effective amount" or "effective amount" of a formulation of the present disclosure may be used to inhibit, block, or reverse the activation, migration, or proliferation of cells or to effectively treat hypertension or ameliorate the symptoms of hypertension.

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

Examples

The following examples are intended to illustrate but not limit the disclosed embodiments.

Example A: Effect of pH on the Formation of Degradants in Lisinopril Formulations at 60° C.

Formulations were prepared containing lisinopril according to Table A-1. The components were dissolved in ~15 mL water then additional water was added to bring each solution to 20 mL. The pH was adjusted to the final value with ~1N HCl or ~0.5N NaOH. Five milliliters of each formulation were transferred to each of four 3-dram glass screw-capped vials with Teflon inserts in the caps. The vials were placed into a 60° C. heating chamber then removed and analyzed by HPLC at times of zero, ~48 and ~145 hours.

TABLE A-1

Formulation (in mg) of Lisinopril Formulations at Varying pH and 50 mM Citrate Buffer

| Component | Formulation | | | | |
| --- | --- | --- | --- | --- | --- |
| | A1 | A2 | A3 | A4 | A5 |
| Lisinopril dihydrate[a] | 21.78 | 21.78 | 21.78 | 21.78 | 21.78 |
| Mannitol | 1000 | 1000 | | 1000 | 1000 |
| Xylitol | | | 1000 | | |
| Citric acid, anhydrous | 153.6 | 107.6 | 107.6 | 107.6 | 61.4 |
| Sodium citrate, dihydrate | 45.6 | 100 | 100 | 100 | 155 |
| Sodium benzoate | 20.0 | 20.0 | 20.0 | 20.0 | 20.0 |
| Methylparaben sodium | | | | 34.4 | |
| Sucralose | 15.0 | 15.0 | 15.0 | 15.0 | 15.0 |
| Sodium chloride | 50.0 | 50.0 | 50.0 | 50.0 | 50.0 |
| Grape flavor (powdered) | 10.0 | 10.0 | 10.0 | 10.0 | 10.0 |
| Water | qs 20 mL | qs 20 mL | qs 20 mL | qs 20 mL | qs 20 mL |
| pH | 3.21 | 4.05 | 4.05 | 4.27 | 4.81 |

[a] = equivalent to 1 mg/mL lisinopril
qs = sufficient quantity

The results of the HPLC analysis for the two main degradants in the samples, lisinopril diketopiperazine and lisinopril hydrolysate, are provided in Table A-2.

TABLE A-2

Primary Degradants Present in the Formulations (% w/w of lisinopril)

| Hours at 60° C. | Formulation | | | | |
|---|---|---|---|---|---|
| | A1 | A2 | A3 | A4 | A5 |
| Lisinopril Diketopiperazine | | | | | |
| 0 | 0.05 | 0.04 | 0.05 | 0.04 | 0.04 |
| 45.5 | 2.51 | 0.78 | 0.74 | 0.46 | 0.20 |
| 145.5 | 7.93 | 2.36 | 2.16 | 1.39 | 0.48 |
| Lisinopril Hydrolysate | | | | | |
| 0 | 0.11 | 0.11 | 0.11 | 0.11 | 0.11 |
| 45.5 | 0.35 | 0.25 | 0.22 | 0.23 | 0.22 |
| 145.5 | 0.85 | 0.54 | 0.46 | 0.50 | 0.48 |

Example B: Stability of Powder and Solution Formulations of Lisinopril

Powder formulations were prepared according to Table B-1. All components in each formulation except mannitol or xylitol were added to a 2.5 L polypropylene screw capped bottle. The bottle was mixed by inversion in a Turbula mixer for 5 minutes. One-half of the mannitol or xylitol was then added, the components mixed for 5 minutes, then the other half of the mannitol or xylitol was added and a final mix of 5 minutes was completed. Five gram aliquots of each formulation were placed into opaque high density polyethylene bottles. The bottles were screw-capped and placed into storage at room temperature (19-23° C.) and at 40° C.±2° C.

One liter of solution formulation was prepared for each formulation by adding 66.67 grams of each powdered formulation to a 1 liter volumetric flask and adding about 500 mL water. The powder was dissolved with mixing then the contents of the flask were brought to 1 L with additional water. Fifty milliliter aliquots of each formulation were placed into HDPE bottles. The bottles were screw-capped and placed into storage at 5° C.±3° C., at room temperature (19-23° C.) and at 40° C.±2° C.

At various times, bottles were removed from the storage condition and analyzed. The powder bottles were constituted with purified water to yield a final volume in each bottle of 75 mL.

TABLE B-1

Formulation of Lisinopril Formulations

| Component | B1 | B2 | B3 | B4 | B5 |
|---|---|---|---|---|---|
| Powder Formulation (grams) | | | | | |
| Lisinopril dihydrate[a] | 10.4 | 10.4 | 10.4 | 10.4 | 3.05 |
| Mannitol | 481.7 | 485.0 | 487.7 | 484.4 | |
| Xylitol | | | | | 141.2 |
| Citric acid, anhydrous | 43.3 | 52.8 | 38.38 | 29.0 | 12.7 |
| Sodium citrate, anhydrous | 65.4 | 52.4 | 71.9 | 84.4 | 19.2 |
| Potassium sorbate | | | 9.57 | 9.57 | |
| Sodium benzoate | 9.57 | 9.57 | | | 2.81 |
| Methylparaben sodium | 11.0 | 11.01 | 3.35 | 3.35 | 3.23 |
| Sucralose | 7.18 | 7.18 | 7.18 | 7.18 | 2.10 |
| Grape flavor (powdered) | 9.57 | 9.57 | 9.57 | 9.57 | 2.81 |
| Total solids | 638.0 | 638.0 | 638.0 | 638.0 | 187.0 |
| Liquid Formulations (mg/mL) | | | | | |
| Lisinopril dihydrate[b] | 1.09 | 1.09 | 1.09 | 1.09 | 1.09 |
| Mannitol | 50.33 | 50.68 | 50.96 | 50.62 | |
| Xylitol | | | | | 50.33 |
| Citric acid, anhydrous | 4.52 | 5.52 | 4.01 | 3.03 | 4.52 |
| Sodium citrate, anhydrous | 6.83 | 5.48 | 7.51 | 8.83 | 6.83 |
| Potassium sorbate | | | 1.00 | 1.00 | |
| Sodium benzoate | 1.00 | 1.00 | | | 1.00 |
| Methylparaben sodium | 1.15 | 1.15 | 0.35 | 0.35 | 1.15 |
| Sucralose | 0.75 | 0.75 | 0.75 | 0.75 | 0.75 |
| Grape flavor (powdered) | 1.00 | 1.00 | 1.00 | 1.00 | 1.00 |
| Purified water | qs | qs | qs | qs | qs |
| Measured pH | 4.7 | 4.3 | 4.8 | 5.2 | 4.7 |

[a] = contained ~8.4% water of hydration to yield 1.0 mg/mL lisinopril upon constitution with water
qs = sufficient quantity
[b] = equivalent to 1 mg/mL lisinopril The results of the HPLC analysis for the diketopiperazine and hydrolysate degradants in the samples are provided in Table B-2.

TABLE B-2

Degradant Content After Storage (% w/w of lisinopril)

| | Storage | | Formulation | | | | |
|---|---|---|---|---|---|---|---|
| | ° C. | Weeks | B1 | B2 | B3 | B4 | B5 |
| Powder Formulations | | | | | | | |
| Diketopiperazine | 19-23 | 0 | <0.05 | <0.05 | <0.05 | <0.05 | <0.05 |
| | | 4 | <0.05 | 0.05 | <0.05 | <0.05 | <0.05 |
| | | 8 | 0.05 | 0.06 | 0.05 | 0.05 | 0.07 |
| | | 12 | 0.07 | 0.07 | <0.05 | <0.05 | |
| | 40 | 0 | <0.05 | <0.05 | <0.05 | <0.05 | <0.05 |
| | | 4 | 0.05 | 0.05 | 0.05 | 0.05 | 0.06 |
| | | 8 | 0.07 | 0.07 | 0.06 | 0.05 | 0.09 |
| | | 12 | 0.10 | 0.10 | 0.09 | 0.07 | |
| Lisinopril hydrolysate | 19-23 | 0 | 0.03 | <0.05 | <0.05 | <0.05 | <0.05 |
| | | 4 | 0.04 | <0.05 | <0.05 | <0.05 | 0.05 |
| | | 8 | 0.05 | 0.05 | <0.05 | <0.05 | 0.05 |
| | | 12 | 0.05 | 0.05 | 0.05 | <0.05 | |
| | 40 | 0 | 0.03 | <0.05 | <0.05 | <0.05 | <0.05 |
| | | 4 | 0.04 | <0.05 | <0.05 | <0.05 | 0.05 |
| | | 8 | 0.05 | 0.05 | 0.05 | 0.05 | 0.05 |
| | | 12 | 0.04 | 0.05 | 0.06 | 0.05 | |

TABLE B-2-continued

Degradant Content After Storage (% w/w of lisinopril)

| | Storage | | Formulation | | | | |
|---|---|---|---|---|---|---|---|
| | °C. | Weeks | B1 | B2 | B3 | B4 | B5 |
| | | | Liquid Formulations | | | | |
| Diketopiperazine | 19-23 | 0 | 0.05 | 0.05 | 0.06 | <0.05 | <0.05 |
| | | 4 | 0.06 | 0.09 | 0.06 | <0.05 | 0.07 |
| | | 8 | 0.09 | 0.13 | 0.07 | 0.05 | 0.10 |
| | | 12 | 0.12 | 0.18 | 0.12 | 0.11 | |
| | 40 | 0 | 0.05 | 0.05 | 0.06 | <0.05 | <0.05 |
| | | 4 | 0.23 | 0.46 | 0.19 | 0.11 | 0.23 |
| | | 8 | 0.42 | 0.87 | 0.35 | 0.15 | 0.46 |
| | | 12 | 0.67 | 1.40 | 0.59 | 0.27 | |
| Lisinopril hydrolysate | 19-23 | 0 | <0.05 | <0.05 | <0.05 | <0.05 | <0.05 |
| | | 4 | <0.05 | <0.05 | 0.05 | <0.05 | 0.05 |
| | | 8 | 0.05 | 0.05 | 0.05 | 0.05 | 0.05 |
| | | 12 | 0.05 | 0.05 | 0.05 | 0.06 | |
| | 40 | 0 | <0.05 | <0.05 | <0.05 | <0.05 | <0.05 |
| | | 4 | 0.08 | 0.08 | 0.10 | 0.07 | 0.13 |
| | | 8 | 0.15 | 0.16 | 0.15 | 0.14 | 0.17 |
| | | 12 | 0.17 | 0.19 | 0.20 | 0.16 | |

Additionally the parabens also reacted with the sugar alcohols (xylitol and mannitol) to create new transesterification degradants.

Example C: Stability of Powder and Solution Formulations of Lisinopril with Alternate Sweeteners Powder formulations were prepared according to Table C-1. All components in each formulation except mannitol or xylitol were mixed in a mortar and pestle then the mannitol or xylitol was added to the mortar in increments with mixing to achieve geometric dilution. The final blend was transferred to a 2.5 L polypropylene screw capped bottle and the bottle was mixed by inversion in a Turbula mixer for 10 minutes. Aliquots (2.4 g) of each formulation were placed into opaque high density polyethylene bottles. The bottles were screw-capped and placed into storage at room temperature (19-23° C.) and at 40° C.±2° C. One liter of solution formulation was prepared for each formulation by adding 60.0 grams of powdered formulation C2 or C3, or 160 g of powdered formula C1 to one liter volumetric flasks and adding about 500 mL water. The powder was dissolved with mixing then the contents of the flasks were brought to 1 L with additional water. Forty milliliter aliquots of each formulation were placed into HDPE bottles. The bottles were screw-capped and placed into storage at room temperature (19-23° C.) and at 40° C.±2° C.

At various times, bottles were removed from the storage condition and analyzed. The powder bottles were constituted with purified water to yield a final volume in each bottle of 40 mL.

TABLE C-1

Formulation of Lisinopril Formulations

| | C1 | C2 | C3 |
|---|---|---|---|
| | Powder Formulations (grams) | | |
| Lisinopril dihydrate[a] | 2.87 | 2.87 | 2.87 |
| Xylitol | 408.1 | 138.34 | |
| Mannitol | | | 136.22 |

TABLE C-1-continued

Formulation of Lisinopril Formulations

| | C1 | C2 | C3 |
|---|---|---|---|
| Citric acid, anhydrous | 2.32 | 2.32 | 2.32 |
| Sodium citrate, anhydrous | 3.70 | 3.70 | 3.70 |
| Sodium benzoate | 2.64 | 2.64 | 2.64 |
| Sodium saccharin | | 5.94 | |
| Sucralose (as Rebalance X60) | | | 7.92 |
| Grape flavor (powdered) | 2.64 | 2.64 | 2.64 |
| Total solids | 422.32 | 158.45 | 158.32 |
| | Liquid Formulations (mg/mL) | | |
| Lisinopril dihydrate[b] | 1.09 | 1.09 | 1.09 |
| Xylitol | 154.60 | 52.4 | |
| Mannitol | | | 51.60 |
| Citric acid, anhydrous | 0.88 | 0.88 | 0.88 |
| Sodium citrate, anhydrous | 1.40 | 1.40 | 1.40 |
| Sodium benzoate | 1.00 | 1.00 | 1.00 |
| Sodium saccharin | | 2.25 | |
| Sucralose (as Rebalance X60) | | | 3.00 |
| Grape flavor (powdered) | 1.00 | 1.00 | 1.00 |
| Purified water | qs | qs | qs |
| Measured pH | 4.8 | 4.8 | 4.8 |

[a]= contained ~8.4% water. Yields 1.0 mg/mL lisinopril upon constitution with water
qs = sufficient quantity
[b]= equivalent to 1 mg/mL lisinopril The results for pH and the HPLC analysis for degradants in the samples are provided in Table C-2.

TABLE C-2

Degradant Content After Storage (% w/w of Lisinopril)

| | Storage | | Formulation | | |
|---|---|---|---|---|---|
| | °C. | weeks | C1 | C2* | C3 |
| | | | Powder Formulations | | |
| Diketopiperazine | 19-23 | 0 | 0.05 | 0.06 | 0.05 |
| | | 4 | 0.05 | 0.10 | <0.05 |
| | | 8 | 0.05 | 0.12 | <0.05 |
| | | 12 | 0.06 | 0.13 | <0.05 |
| | | 26 | 0.08 | 0.15 | 0.05 |
| | 40 | 0 | 0.05 | 0.06 | 0.05 |
| | | 4 | 0.12 | 0.23 | 0.08 |

TABLE C-2-continued

Degradant Content After Storage (% w/w of Lisinopril)

| | Storage | | Formulation | | |
|---|---|---|---|---|---|
| | °C. | weeks | C1 | C2* | C3 |
| | | 8 | 0.19 | 0.40 | 0.12 |
| | | 12 | 0.21 | 0.49 | 0.11 |
| | | 26 | 0.27 | 0.66 | 0.16 |
| Lisinopril hydrolysate | 19-23 | 0 | 0.06 | | 0.05 |
| | | 4 | 0.05 | | 0.05 |
| | | 8 | <0.05 | | 0.05 |
| | | 12 | <0.05 | | <0.05 |
| | | 26 | 0.05 | | 0.05 |
| | 40 | 0 | 0.06 | | 0.05 |
| | | 4 | 0.05 | | 0.05 |
| | | 8 | 0.05 | | 0.05 |
| | | 12 | 0.05 | | 0.05 |
| | | 26 | 0.05 | | 0.05 |
| Liquid Formulations | | | | | |
| Diketopiperazine | 19-23 | 0 | <0.05 | 0.05 | 0.05 |
| | | 4 | 0.05 | 0.08 | 0.06 |
| | | 8 | 0.05 | 0.11 | 0.06 |
| | | 12 | 0.06 | 0.11 | 0.06 |
| | | 26 | 0.10 | 0.14 | 0.10 |
| | 40 | 0 | <0.05 | 0.05 | 0.05 |
| | | 4 | 0.16 | 0.20 | 0.17 |
| | | 8 | 0.30 | 0.34 | 0.30 |
| | | 12 | 0.45 | 0.49 | 0.45 |
| | | 26 | 0.87 | 0.90 | 0.83 |
| Lisinopril hydrolysate | 19-23 | 0 | 0.05 | | 0.05 |
| | | 4 | <0.05 | | 0.05 |
| | | 8 | 0.05 | | 0.05 |
| | | 12 | 0.05 | | 0.05 |
| | | 26 | 0.06 | | 0.06 |
| | 40 | 0 | 0.05 | | 0.05 |
| | | 4 | 0.08 | | 0.09 |
| | | 8 | 0.12 | | 0.13 |
| | | 12 | 0.19 | | 0.19 |
| | | 26 | 0.36 | | 0.36 |

*Hydrolysate could not be quantitated in the presence of saccharin

Example D: Antimicrobial Effectiveness Testing at pH 4.8

Lisinopril formulations were prepared containing differing amounts of the antimicrobial preservative, sodium benzoate. The formulations were then tested for antimicrobial effectiveness (AET) according to the procedures in the 2014 United States Pharmacopeia 37, Chapter <51> for category 3 products. The formulation of the formulations and the AET results are included in Table D-1.

TABLE D-1

Formulation and AET Testing Results

| | Formulation | | | | |
|---|---|---|---|---|---|
| | D1 | D2 | D3 | D4 | D5 |
| Formulation (mg/mL) | | | | | |
| Lisinopril dihydrate[a] | 1.089 | 1.089 | 1.089 | 1.089 | 1.089 |
| Xylitol | 155 | 155 | 155 | 155 | 155 |
| Citric acid anhydrous | 0.88 | 0.88 | 0.88 | 0.88 | 0.88 |
| Sodium citrate anhydrous | 1.40 | 1.40 | 1.40 | 1.40 | 1.40 |
| Sodium benzoate | 1.00 | 0.80 | 0.60 | 0.40 | 0.20 |
| Grape Flavor | 1.00 | 1.00 | 1.00 | 1.00 | 1.00 |
| Water | qs | qs | qs | qs | qs |
| HCl/NaOH | as needed to achieve pH | | | | |
| Measured pH | 4.8 | 4.8 | 4.8 | 4.8 | 4.8 |
| AET Results | | | | | |
| USP <51> | Pass | Pass | Pass | Fail | Fail |

[a] = equivalent to 1 mg/mL lisinopril

Example E: Antimicrobial Effectiveness Testing at pH 5.0 and 5.1

Formulations were prepared containing differing amounts of the antimicrobial preservative, sodium benzoate and at pH values of 5.0 or 5.1. The formulations were then tested for antimicrobial effectiveness (AET) according to the procedures in the 2015 United States Pharmacopeia 38, Chapter <51> for category 3 products. The formulation of the formulations and the AET results are included in Table E-1.

TABLE E-1

Formulation and AET Testing Results

| | Formulation | | | | | |
|---|---|---|---|---|---|---|
| | E1 | E2 | E3 | E4 | E5 | E6 |
| Formulation (mg/mL) | | | | | | |
| Lisinopril dihydrate[a] | 1.089 | 1.089 | 1.089 | 1.089 | 1.089 | 1.089 |
| Xylitol | 150.0 | 150.0 | 150.0 | 150.0 | 150.0 | 150.0 |
| Citric acid anhydrous | 0.86 | 0.86 | 0.86 | 0.86 | 0.86 | 0.86 |
| Sodium citrate anhydrous | 1.43 | 1.43 | 1.43 | 1.43 | 1.43 | 1.43 |
| Sodium benzoate | 0.80 | 0.76 | 0.72 | 0.68 | 0.64 | 0.72 |
| Water | qs | qs | qs | qs | qs | qs |
| HCl/NaOH | as needed to achieve pH | | | | | |
| Measured pH | 5.0 | 5.0 | 5.0 | 5.0 | 5.0 | 5.1 |
| AET Results | | | | | | |
| USP <51> | Pass | Pass | Pass | Pass | Pass | Pass |

[a] equivalent to 1 mg/mL lisinopril

Example F: Stability of Solution Formulations of Lisinopril

Solution formulations were prepared according to Table F-1. The components were dissolved in about 80% of the final volume of water then additional water was added to bring the solution to final volume. The pH was adjusted to the target pH with hydrochloric acid or sodium hydroxide The solutions were dispensed into HDPE bottles, 40 mL of formulations F1-F6 into 75 mL bottles, and 150 mL of formulation F7 into 150 mL bottles. The bottles were screw-capped and placed into controlled condition storage at 5° C.±3° C., room temperature (19-23° C.) and at 40° C.±2° C. At various times, bottles were removed from the storage condition and analyzed. The results are shown in Table F-2.

TABLE F-1

Formulation (mg/mL) of Lisinopril Ready to Use Liquid Formulations

| | Formulation | | | | | | |
|---|---|---|---|---|---|---|---|
| | F1 | F2 | F3 | F4 | F5 | F6 | F7 |
| Lisinopril dihydrate[a] | 1.09 | 1.09 | 1.09 | 1.09 | 1.09 | 1.09 | 1.09 |
| Xylitol | 150.0 | 150.0 | | 150.0 | | 100.0 | 150.0 |
| Citric acid anhydrous | 1.92 | 1.92 | 1.92 | 1.92 | 1.92 | 1.92 | 0.86 |
| Sodium citrate anhydrous | | | | | | | 1.44 |
| Sodium benzoate | 0.80 | 0.80 | 0.80 | | | | 0.80 |
| Methylparaben sodium | | | | 1.72 | 1.72 | 1.72 | |
| Propylparaben sodium | | | | 0.17 | 0.17 | 0.17 | |
| Glycerin | | 10.0 | | | | | |
| Saccharin sodium | | | | | | 2.00 | |
| Sucralose USP | | | | 2.00 | 2.00 | | |
| Water | qs 1 mL | qs 1 mL | qs 1 mL | qs 1 mL | qs 1 mL | qs 1 mL | qs 1 mL |
| HCl/NaOH | | | as needed to achieve pH | | | | |
| Target pH | 4.8 | 4.8 | 4.8 | 5.2 | 5.2 | 5.2 | 5.0 |

[a]equivalent to 1 mg/mL lisinopril

TABLE F-2

Degradant Content After Storage (% w/w of Lisinopril)

| Storage | | Formulation | | | | | | |
|---|---|---|---|---|---|---|---|---|
| ° C. | weeks | F1 | F2 | F3 | F4 | F5 | F6* | F7 |
| | | Lisinopril Diketopiperazine | | | | | | |
| 19-23 | 0 | <0.05 | 0.05 | 0.05 | 0.05 | 0.06 | 0.05 | <0.05 |
| | 4 | 0.05 | 0.05 | 0.05 | <0.05 | <0.05 | 0.07 | <0.05 |
| | 8 | 0.07 | 0.06 | 0.06 | <0.05 | <0.05 | 0.08 | 0.05 |
| | 12 | 0.07 | 0.07 | 0.07 | 0.06 | 0.06 | 0.06 | 0.05 |
| | 26 | 0.12 | 0.12 | 0.11 | 0.09 | 0.08 | 0.09 | 0.07 |
| | 52 | 0.17 | 0.17 | 0.16 | 0.12 | 0.09 | 0.11 | |
| 40 | 0 | <0.05 | 0.05 | 0.05 | 0.05 | 0.06 | 0.05 | <0.05 |
| | 4 | 0.20 | 0.21 | 0.20 | 0.10 | 0.10 | 0.12 | 0.14 |
| | 8 | 0.39 | 0.35 | 0.33 | 0.18 | 0.14 | 0.18 | 0.27 |
| | 12 | 0.51 | 0.49 | 0.45 | 0.25 | 0.22 | 0.23 | 0.36 |
| | 26 | 1.13 | 1.11 | 1.04 | 0.56 | 0.49 | 0.54 | 0.71 |
| | 52 | 1.93 | 1.89 | 1.72 | 0.90 | 0.83 | 0.89 | |
| | | Lisinopril Hydrolysate | | | | | | |
| 19-23 | 0 | 0.05 | <0.05 | 0.05 | 0.06 | <0.05 | | 0.05 |
| | 4 | 0.05 | 0.05 | 0.05 | 0.06 | 0.06 | | 0.05 |
| | 8 | 0.05 | 0.05 | 0.06 | 0.05 | 0.05 | | <0.05 |
| | 12 | 0.05 | 0.05 | 0.05 | 0.04 | 0.05 | | <0.05 |
| | 26 | 0.07 | 0.07 | 0.07 | 0.06 | 0.07 | | 0.05 |
| | 52 | 0.08 | 0.08 | 0.08 | 0.06 | 0.08 | | |
| 40 | 0 | 0.05 | <0.05 | 0.05 | 0.06 | <0.05 | | 0.05 |
| | 4 | 0.11 | 0.11 | 0.11 | 0.08 | 0.10 | | 0.11 |
| | 8 | 0.17 | 0.16 | 0.16 | 0.11 | 0.14 | | 0.13 |

TABLE F-2-continued

Degradant Content After Storage (% w/w of Lisinopril)

| Storage | | Formulation | | | | | | |
|---|---|---|---|---|---|---|---|---|
| ° C. | weeks | F1 | F2 | F3 | F4 | F5 | F6* | F7 |
| | 12 | 0.18 | 0.18 | 0.18 | 0.12 | 0.17 | | 0.18 |
| | 26 | 0.45 | 0.46 | 0.49 | 0.31 | 0.44 | | 0.36 |
| | 52 | 0.87 | 0.89 | 0.91 | 0.62 | 0.84 | | |

*Hydrolysate could not be quantitated in the presence of saccharin

Example G: Lisinopril Formulation at Higher pH

A solution formulation was prepared at pH 8.0 according to Table G-1. The components were dissolved in about 80% of the final volume of water then additional water was added to bring the solution to final volume. The pH was adjusted to the target pH with hydrochloric acid or sodium hydroxide.

TABLE G-1

Formulation of Lisinopril Ready to Use Liquid Formulation at Higher pH

| Component | mg/mL |
|---|---|
| Lisinopril dihydrate[a] | 1.09 |
| Monobasic sodium phosphate anhydrous | 2.40 |
| Methylparaben sodium | 1.72 |
| Propylparaben sodium | 0.225 |
| Sucralose USP | 0.70 |
| Water | qs |
| HCl/NaOH | as needed to achieve pH |
| Target pH | 8.0 |

[a] = equivalent to 1 mg/mL lisinopril

Example H: Lisinopril Formulation Containing Less Sucralose

A solution formulation was prepared according to Table H-1. The components were dissolved in about 80% of the final volume of water then additional water was added to bring the solution to final volume. The pH was adjusted to the target pH with hydrochloric acid or sodium hydroxide.

TABLE H-1

Formulation of Lisinopril Ready to Use Liquid Formulation With less Sucralose

| Component | mg/mL |
|---|---|
| Lisinopril dihydrate[a] | 1.09 |
| Citric acid anhydrous | 0.86 |
| Sodium citrate anhydrous | 1.44 |
| Sodium benzoate | 0.80 |
| Sucralose USP | 0.70 |
| Water | qs |
| HCl/NaOH | as needed to achieve pH |
| pH | 4.9 |

[a] = equivalent to 1 mg/mL lisinopril

Example I: Clinical Trial: Bioavailability Study of 10 mg Lisinopril Oral Solution vs. Zestril® 10 mg Tablets Under Fasted Conditions The objective of this open-label, randomized, two period, two treatment crossover study was to compare the oral bioavailability of a test formulation of 10 mL of lisinopril oral solution, 1 mg/M1 (formulation F-7), to an equivalent oral dose of the commercially available comparator product, Zestril® lisinopril 10 mg tablet, when administered under fasted conditions in healthy adults.

Study design: Fifty-six healthy adult subjects received a single 10 mL dose of lisinopril oral solution, 1 mg/mL, formulation F-7 (Treatment A), in one period and a separate single dose of Zestril 10 mg tablet (Treatment B) in another period. Screening assessments were performed by the investigator or designee within 28 days prior to study start. Each treatment was administered after an overnight fast of at least 10 hours. Treatment A was administered via a 10 mL oral dosing syringe and followed with 240 mL of room temperature tap water. Treatment B was administered with 240 mL of room temperature tap water. The subjects fasted for 4 hours after dosing. Except for the 240 mL of room temperature water provided with the dose, no water was consumed for 1 hour prior through 1 hour postdose. Each drug administration was separated by a washout period of at least 7 days.

During each study period, meals were the same and scheduled at approximately the same times relative to dose. In addition, during each period, blood samples were obtained prior to and following each dose at selected times through 96 hours postdose. Pharmacokinetic samples were analyzed for lisinopril using a validated analytical method; appropriate pharmacokinetic parameters were calculated for each formulation using non-compartmental methods. Blood was also drawn and urine collected for clinical laboratory testing at screening and at the end of the study.

Statistical Methods: The concentration-time data were analyzed using noncompartmental methods in Phoenix™ WinNonlin® (Version 6.3, Pharsight Corporation). Concentration-time data that were below the limit of quantitation (BLQ) were treated as zero in the data summarization and descriptive statistics. In the pharmacokinetic analysis, BLQ concentrations were treated as zero from time-zero up to the time at which the first quantifiable concentration was observed; embedded and/or terminal BLQ concentrations were treated as "missing". Actual sample times were used for all pharmacokinetic and statistical analyses. Analysis of variance (ANOVA) and the Schuirmann's two one-sided t-test procedures at the 5% significance level were applied to the log-transformed pharmacokinetic exposure parameters, $C_{max}$, $AUC_{last}$, and $AUC_{inf}$. The 90% confidence interval for the ratio of the geometric means (Test/Reference) was calculated. Bioequivalence was declared if the lower and upper confidence intervals of the log-transformed parameters were within 80% to 125%.

Results: Based on the geometric mean ratios of lisinopril AUCs (Test/Reference for $AUC_{last}$ and $AUC_{inf}$), the bioavailability of the test formulation relative to the reference product was approximately 94% to 95%. The geometric mean ratio of lisinopril $C_{max}$ was 94.11%. The 90% confidence intervals about the geometric mean ratios (Test/

Reference) of lisinopril $C_{max}$ and AUCs were within the accepted 80% to 125% range, indicating no significant difference.

Example J: Clinical Trial: Bioavailability Study of 10 mg Lisinopril Oral Solution vs. Zestril® 10 mg Tablets Under Fed Conditions This study was conduct the same as in example G, with the exceptions that only 52 subjects were analyzed for pharmacokinetic parameters, and the dose administration followed a 10-hour overnight fast, followed by the ingestion of a Food and Drug Administration standard high-calorie, high-fat breakfast meal.

Results: Based on the geometric mean ratios of lisinopril AUCs (Test/Reference for $AUC_{last}$ and $AUC_{inf}$), the bioavailability of the test formulation relative to the reference product was approximately 99% to 101%. The geometric mean ratio of lisinopril $C_{max}$ was 99.45%. The 90% confidence intervals about the geometric mean ratios (Test/Reference) of lisinopril $C_{max}$ and AUCs were within the accepted 80% to 125% range, indicating no significant difference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating hypertension in a subject comprising administering to that subject a therapeutically effective amount of a stable oral liquid formulation, comprising:
   (i) about 1 mg/ml lisinopril or a pharmaceutically acceptable salt or solvate thereof;
   (ii) a sweetener;
   (iii) a buffer comprising citric acid and sodium citrate;
   (iv) a preservative selected from the group consisting of sodium benzoate, benzoic acid, sorbic acid, methylparaben, propylparaben, and salts thereof; and
   (v) water;
   wherein the formulation is stable at about 25±5° C. for at least 6 months.
2. The method of claim 1, wherein the lisinopril is lisinopril dihydrate.
3. The method of claim 1, wherein the pH of the formulation is between about 4 and about 5.2.
4. The method of claim 1, wherein the formulation is stable at about 25±5° C. for at least 24 months.
5. The method of claim 1, wherein the hypertension is primary (essential) hypertension.
6. The method of claim 1, wherein the hypertension is secondary hypertension.
7. The method of claim 1, wherein the subject has blood pressure values greater than or equal to 140/90 mmm Hg.
8. The method of claim 1, wherein the subject is elderly.
9. The method of claim 1, wherein the subject is a child.
10. The method of claim 1, wherein the formulation is further administered in combination with an agent selected from the group consisting of diuretics, beta blockers, alpha blockers, mixed alpha and beta blockers, calcium channel blockers, angiotensin II receptor antagonists, ACE inhibitors, aldosterone antagonists, and alpha-2 agonists.
11. A method of treating heart failure in a subject comprising administering to that subject a therapeutically effective amount of a stable oral liquid formulation, comprising:
    (i) about 1 mg/ml lisinopril or a pharmaceutically acceptable salt or solvate thereof;
    (ii) a sweetener;
    (iii) a buffer comprising citric acid and sodium citrate;
    (iv) a preservative selected from the group consisting of sodium benzoate, benzoic acid, sorbic acid, methylparaben, propylparaben, and salts thereof; and
    (v) water;
    wherein the formulation is stable at about 25±5° C. for at least 6 months.
12. The method of claim 11, wherein the lisinopril is lisinopril dihydrate.
13. The method of claim 11, wherein the pH of the formulation is between about 4 and about 5.2.
14. The method of claim 11, wherein the formulation is stable at about 25±5° C. for at least 24 months.
15. The method of claim 11, wherein the subject is not responding adequately to diuretics and *digitalis*.
16. A method of treating a hemodynamically stable subject within 24 hours of acute myocardial infarction comprising administering to that subject a therapeutically effective amount of a stable oral liquid formulation, comprising:
    (i) about 1 mg/ml lisinopril or a pharmaceutically acceptable salt or solvate thereof;
    (ii) a sweetener;
    (iii) a buffer comprising citric acid and sodium citrate;
    (iv) a preservative selected from the group consisting of sodium benzoate, benzoic acid, sorbic acid, methylparaben, propylparaben, and salts thereof; and
    (v) water;
    wherein the formulation is stable at about 25±5° C. for at least 6 months.
17. The method of claim 16, wherein the lisinopril is lisinopril dihydrate.
18. The method of claim 16, wherein the pH of the formulation is between about 4 and about 5.2.
19. The method of claim 16, wherein the formulation is stable at about 25±5° C. for at least 24 months.
20. The method of claim 16, wherein the formulation is further administered in combination with an agent selected from the group consisting of beta blockers, aspirin, and thrombolytics.

* * * * *